United States Patent
Aschenbrenner et al.

(10) Patent No.: US 6,949,567 B2
(45) Date of Patent: Sep. 27, 2005

(54) COMPOUNDS FOR THE TREATMENT OF PROTOZOAL DISEASES

(75) Inventors: Andrea Aschenbrenner, München (DE); Katharina Aulinger Fuchs, Neuried (DE); Matthias Dormeyer, München (DE); Gabriel Garcia, München (DE); Bernd Kramer, Aachen (DE); Jürgen Kraus, Starnberg (DE); Rolf Krauss, Planegg-Martinsried (DE); Johan Leban, München (DE); Stefano Pegoraro, Planegg-Martinsried (DE); Wael Saeb, Planegg-Martinsried (DE); Kristina Wolf, München (DE)

(73) Assignee: 4SC AG, Planegg-Martinsried (DE)

(*) Notice: Subject to any disclaimer, the term of this patent is extended or adjusted under 35 U.S.C. 154(b) by 262 days.

(21) Appl. No.: 10/083,008

(22) Filed: Feb. 26, 2002

(65) Prior Publication Data

US 2003/0119876 A1 Jun. 26, 2003

Related U.S. Application Data

(63) Continuation-in-part of application No. 10/020,683, filed on Dec. 12, 2001, now abandoned.

(30) Foreign Application Priority Data

Feb. 26, 2001 (DE) .......................................... 101 09 204

(51) Int. Cl.[7] ..................... C07D 413/12; C07C 275/30; C07C 275/28; A61K 31/17; A61P 33/02
(52) U.S. Cl. ...................... 514/309; 514/311; 514/378; 514/586; 514/597; 514/603; 514/621; 514/237.8; 514/357; 514/385; 514/408; 514/471; 546/171; 546/141; 546/264; 548/248; 548/306; 548/349.1; 548/567; 548/190; 548/233; 548/312.7; 564/27; 564/79; 564/238; 564/239; 564/49; 564/50; 544/159; 544/162; 544/238; 544/295; 544/296; 544/405; 549/77
(58) Field of Search ................................ 546/171, 141; 548/248, 306, 349.1, 567; 564/27, 79, 238, 239, 49, 50; 544/159, 162; 549/77; 514/311, 309, 378, 586, 597, 603, 621, 237.5, 357, 385, 405, 471

(56) References Cited

U.S. PATENT DOCUMENTS

| | | | |
|---|---|---|---|
| 2,762,742 A | 9/1956 | O'Neill et al. .............. | 167/53.1 |
| 3,529,982 A | 9/1970 | Luethi et al. ................ | 106/178 |
| 4,003,875 A | 1/1977 | Luthi et al. ................. | 260/45.9 |
| 4,405,644 A | 9/1983 | Kabbe et al. ............... | 424/322 |
| 4,546,113 A | 10/1985 | Glazer ........................ | 514/636 |
| 5,780,483 A | 7/1998 | Widdowson et al. ....... | 514/311 |
| 6,180,675 B1 | 1/2001 | Widdowson et al. ....... | 514/586 |

FOREIGN PATENT DOCUMENTS

| | | |
|---|---|---|
| DE | 1 445 186 | 10/1968 |
| DE | 23 34 355 | 1/1975 |
| DE | 29 28 485 | 1/1981 |
| EP | 0 507 732 B1 | 4/1995 |
| EP | 0 990 646 A1 | 4/2000 |
| GB | 755036 | 8/1956 |
| GB | 888965 | 2/1962 |
| WO | WO 94/22807 | 10/1994 |
| WO | WO 95/01168 | 1/1995 |
| WO | WO 95/23132 | 8/1995 |
| WO | WO 96/25157 | 8/1996 |
| WO | WO 96/39382 | 12/1996 |
| WO | WO 97/29743 | 8/1997 |
| WO | WO 98/24785 | 6/1998 |
| WO | WO 98/52558 | 11/1998 |
| WO | WO 99/05096 | 2/1999 |
| WO | WO 99/06354 | 2/1999 |
| WO | WO 99/32110 | 7/1999 |
| WO | WO 99/32463 | 7/1999 |
| WO | WO 99/37666 | 7/1999 |
| WO | WO 00/72840 A1 | 12/2000 |
| WO | WO 00/78726 A1 | 12/2000 |
| WO | WO 01/36383 A1 | 5/2001 |

OTHER PUBLICATIONS

Adams et al., "Proteasome Inhibitors: A Novel Class of Potent and Effective Antitumor Agents," *Cancer Research* 59:2615–2622 (1999).

Adams et al., "Proteasome Inhibition: A New Stratgey in Cancer Treatment," *Investigational New Drugs* 18:109–121 (2000).

Agejas et al., "A Straightforward Synthesis of 4–Substituted 3,4–Dihydro–1 H–2,1,3–Benzothiadiazine 2,2–Dioxides," *Tetrahedron Letters* 41:9819–9823 (2000).

Alig et al., "Low Molecular Weight, Non–Peptide Fibrinogen Receptor Antagonists," *J. Med. Chem.* 35:4393–4407 (1992).

(Continued)

Primary Examiner—Mark L. Berch
Assistant Examiner—Kahsay Habte
(74) Attorney, Agent, or Firm—Clark & Elbing LLP

(57) ABSTRACT

The invention relates to new diphenylurea having the formula (I)

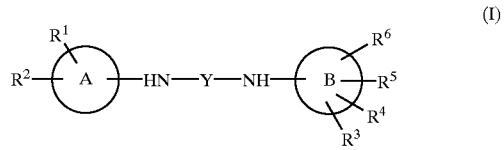

or a salt thereof, where
  Y is C=O, C=S, C=NH, (C=O)$_2$ or SO$_2$;
and to processes for the preparation of these compounds and to their use in the treatment of protozoal diseases and to diseases where the inhibition of intracellular protein-degradation pathways is of benefit.

7 Claims, No Drawings

OTHER PUBLICATIONS

Anastassiadou et al., "Synthesis and Pharmacological Evaluation of Imidazoline Site 11 and 12 Selective Ligands," *Bioorganic & Medicinal Chemistry* 9:585–592 (2001).

Batey et al., "An Efficient New Protocol for the Formation of Unsymmetrical Tri–and Tetrasubstituted Ureas," *Tetrahedron Letters* 39:6267–6270 (1998).

Caronna et al., "Nuclear Transformations by Hydrogenolysis: Synthesis of Pyrimidinones From Isoxazoles Derivatives," *Heterocycles* 24:1377–1380 (1986).

Dewynter et al., "Sulfonyl Bis–N–Oxazolidinone (SBO): A New Versatile Dielectrophile with Sequential Reactivity," *Tetrahedron Letters* 38:8691–8694 (1997).

Dixit et al., "The Use of Polymer Supports in Organic Synthesis. 17. The Synthesis of Unsymmetrical Diamides and Monoamide Monotosylamides From Symmetrical Diamines," *Israel Journal of Chemistry* 17:248–252 (1978).

Dougherty et al., "Ring–Closing Metathesis Strategies to Cyclic Sulfamide Peptidomimetics," *Tetrahedron* 56:9781–9790 (2000).

Dressman et al., "Solid Phase Synthesis of Hydantoins Using a Carbamate Linker and a Novel Cyclization/Cleavage Step," *Tetrahedron Letters* 37:937–940 (1996).

Gautier et al., "Preparation and Synthetic Uses of Amidines," *The Chemistry of Amidines and Imidates* (Chapter 7) pp. 283–348 (1975).

Gomez et al., "An Efficient Procedure for Traceless Solid–Phase Synthesis of N,N'–Substituted Thioureas by Thermolytic Cleavage of Resin–Bound Dithiocarbamates," *J. Comb. Chem.* 2:75–79 (2000).

Gould, "Salt Selection for Basic Drugs," *International Journal of Pharmaceutics* 33:201–217 (1986).

Harger et al., "Migration of the Amino Group in the Base–Induced Rearrangements of N–(Aminophosphinoyl)–O–Sulphonylhydroxylamines," *J. Chem. Soc. Perkin Trans.* 1:2169–2172 (1986).

Houben–Weyl et al., "Kohlensaure–Derivate (Carbonic Acid Derivatives)," Editor Hagemann, Georg Thieme Verlag Stuttgart E4:334–357 (1983).

Houben–Weyl et al., "Kohlensaure–Derivate (Carbonic Acid Derivatives)," Editor Hagemann, Georg Thieme Verlag Stuttgart E4:484–519 (1983).

Houlihan et al., "Halogenated Mazindol Analogs as Potential Inhibitors of the Cocaine Binding Site at the Dopamine Transporter," *J. Med. Chem.* 39:4935–4941 (1996).

Hurd et al., "The Preparation and Chemical Properties of Thionamides," *Chem. Rev.* 61:45–86 (1961).

"Organic Synthesis on Solid Phase" Ed. F.Z. Dorwald pp. 246–247 (1999).

Kalogeris et al., "Selective Proteasome Inhibitors as Anti–Inflammatory Agents," *Exp. Opin. Invest. Drugs* 8:1397–1407 (1999).

Katz et al., "A Novel Serine Protease Inhibition Motif Involving a Multi–Centered Short Hydrogen Bonding Network at the Active Site," *J. Mol. Biol.* 307:1451–1486 (2001).

Lila et al., "Large Scale Preparation of Protected 4–Aminomethylbenzamidine, Application to the Synthesis of the Thrombin Inhibitor, Melagatran," *Synthetic Communications* 28:4419–4429 (1998).

March, "Reactions, Mechanisms, and Structure," *Advanced Organic Chemistry* pp. 396–397 (1992).

Mohan et al., "Solid–Phase Synthesis of N–Substituted Amidinophenoxy Pyridines as Factor XA Inhibitors," *Bioorganic & Medicinal Chemistry Letters* 8:1877–1882 (1998).

Parlow et al., "Utility of Complementary Molecular Reactivity and Molecular Recognition (CMR/R) Technology and Polymer–Supported Reagents in the Solution–Phase Synthesis of Heterocyclic Carboxamides," *J. Org. Chem.* 62:5908–5919 (1997).

Pons et al., "A Constrained Diketopiperazine as a New Scaffold for the Synthesis of Peptidomimetics," *Eur. J. Org. Chem.*, pp. 853–859 (1998).

Presnell et al., "Oxyanion–Mediated Inhibition of Serine Proteases," *Biochemistry* 37:17068–17081 (1998).

Saha et al., "1.1'–Carbonybis (3–Methylimidazolium) Triflate: An Efficient Reagent for Aminoacylations," *J. Am. Chem. Soc.* 111:4856–4859 (1989).

Scarborough et al., "Platelet Glycoprotein IIb–IIIa Antagonists as Prototypical Integrin Blockers: Novel Parenteral and Potential Oral Antithrombotic Agents," *J. Med. Chem.* 43:3453–3473 (2000).

Scheibye et al., "Studies on Organophosphorus Compounds XXI. The Dimer of p–Methoxyphenylthionophosphine Sulfide as Thiation Reagent, a New Route to Thiocarboxamides," *Bull. Soc. Chim. Belg.* 87:229–238 (1978).

Theodoridis, "Nitrogen Protecting Groups: Recent Developments and New Applications," *Tetrahedron* 56:2339–2358 (2000).

Wright et al., "Synthesis and Evaluation of Cryptolepine Analogues for Their Potenital as New Antimalarial Agents," *J. Med. Chem.* 44:3187–3194 (2001).

Organic Synthesis 62:158–161 (1984).

Khim.–Farm. Zh. 8(6):17–20, Abstract (Chem. Abs. 81:91191) (1974).

Bull. Soc. Chim. Fr., (1):376–382, Abstract (Chem. Abs. 69:10170) (1968).

*Organic Synthesis on Solid Phase*, Ed. F.Z. Dorwald pp. 331–335 (1999).

Chih et al., "Mammalian Tissue Trypsin–Like Enzymes: Substrate Specificity and Inhibitory Potency of Substituted Isocoumarin Mechanisms–Based Inhibitors, Benzamidine Derivatives, and Arginine Fluoroalkyl Ketone Transition–State Inhibitors," *Arch. Biochem. Biophys.* 316:808–814, Abstract (1995).

Winkelmann et al., "Tuberculostatic 1,3–diarylthioureas. I," *Abstract & Arzneim.–Forsch* 19:543–558, Abstract (1969).

Wagner et al., *Arzneimittel. Forsch.*, 19:719–730, Abstract (1969).

Ozaki et al., "Preparation of 3,5–Diphenyl–1–1,2,4–Triazole Derivatives as Insecticides and Acaricides," JP 08 092224, Abstract (1996).

Edgar et al., "Leishmania Donovani, Plasmodium Berghei, Trypanosoma Rhodesiense: Antiprotozoal Effects of Some Amidine Types," *Exp. Parasitol.* 52:404–413, Abstract (1981).

Prouty et al., "Effects of Protease Inhibitors on Protein Breakdown in *Escherichia Coli,*" *J. Biol. Chem.* 247:3341–3352, Abstract (1972).

Wojciech et al., "Synthesis of 2–Anilino–3–Aryl–4–Quinazolones," *Dissertationes Pharm.* 17:195–203, Abstract (1965).

Chemical Abstracts 130:77828.

COMPOUNDS FOR THE TREATMENT OF PROTOZOAL DISEASES

This application is a continuation-in-part (CIP) of U.S. Appl. No. 10/020,683, filed Dec. 12, 2001, abandoned, which claims benefit of German Application No. DE 101 09 204.0, filed Feb. 26, 2001.

The present invention relates to compounds which are suitable for the therapy of diseases that can be treated by modulating cellular pathways in eukaryotes as for instance cancer, immunological or inflammatorial disorders as well as infections caused by protozoa (e.g. in malaria caused by plasmodian parasites), and to processes for the preparation of these compounds, and to their use.

DE-A-2 334 355 discloses diphenylurea derivatives which are employed as medicaments against protozoa, in particular against coccidiosis, as said to be superior to the action of 4,4'-dinitrodiphenylurea (nicarbazine), which is furthermore known. DE-A-2 928 485 discloses urea derivatives which are employed for the treatment of disorders of lipid metabolism, WO 96/39382 discloses similar urea derivatives which are employed for treating 5-HT mediated diseases and WO 97/29743, U.S. Pat. No. 5,780,483 discloses similar urea derivatives which are employed for the treatment of diseases mediated by chemokines. GB 888,965 discloses certain diamidines which are employed for the treatment of protozoal diseases, in particular of babesiasis. The synthesis of certain benzamidines is disclosed in Biochemistry, 1998, 37(48), 17068–81, in Khim.-Farm. Zh., 1974, 8(6), 17–20, and in Bull. Soc. Chim. Fr., 1968, (1), 376–82. Other relevant literature is U.S. Pat. No. 6,180,675, WO 99/06354, WO 96/25157, WO 99/32463, WO 98/52558, WO 99/32110, GB 755036, U.S. Pat. No. 2,762,742, U.S. Pat. No. 4,405,644, WO 00/72840 and WO 94/22807.

Many severe diseases are etiologically caused by uncontrolled or unappropriate proliferation of cells ("hyperproliferation"). Depending on the nature of the cells this hyperproliferation can cause as various diseases as cancer, immunological disorders, infectious diseases or others. For many of the disorders caused by or accompanied by hyperproliferative effects adequate treatments are still not available or the emergence of resistance phenomena reduces the efficacy of established drugs significantly.

In cancer uncontrolled cell division leads to anormalous progression of malignant cells and the formation of tumors. Especially in the Western hemisphere cancer is one of the major causes of death. Most of the currently available chemotherapy treatments of cancer are hampered by low efficacy and critical toxicity mostly due to non sufficient selectivity towards the malignant tumor versus normal tissue. Furthermore primary and secondary resistance phenomena limit the clinical success of established chemotherapeutic agents.

Immunological disorders are another example for diseases that are accompanied by hyperproliferative effects. These can be caused by very different triggering factors as for example an unappropriate reaction toward an antigen as in allergic reactions or a misguided stimulus of the immune system by self antigens in autoimmune diseases. Protozoal infections, as malaria in humans or coccidosis in birds, are characterized by hyperproliferation of the infectious agent independent if the parasites live intracellularly or extracellularly of their respective host cells. Malaria represents a major health problem especially in tropical and subtropical countries with hundreds of millions of people being infected. Drugs which are employed against malaria are becoming increasingly ineffective due to spreading resistance of the parasites. Accordingly, there is an urgent need for novel medicaments for the prophylactic and curative treatment of malaria However the development of novel medicaments against malaria has proven to be very difficult.

Other important pathological conditions involving hyperproliferation of cells include restenosis after the angioplasty of artherosclerotic vessels (endothelial cells) or psoriasis (epithelial cells).

One attractive approach to treat hyperproliferative diseases is to modulate essential cellular pathways as those involved in cell activation, metabolism, proliferation, differentiation and maturation or pathways that might lead to cell death as in necrosis or apoptosis.

The objects on which the invention was based therefore consists in providing novel compounds which are suitable for the treatment of diseases as hyperproliferative diseases that can be treated via the modulation of cellular pathways essential for cell activation, metabolism, proliferation, differentiation and maturation or pathways that might lead to cell death as in necrosis or apoptosis, as for instance intracellular protein degradation pathways. These diseases include for example cancer, infections caused by protozoa, in particular for the treatment of malarial diseases, or inflammatorial diseases.

Surprisingly, it has been found that asymmetric urea, guanidine, sulphamide, thiourea and oxalamide derivatives which are substituted by two aromatic hydrocarbon groups, of which one carries an amidine group that can optionally be substituted or cyclic and the other one a group capable of hydrogen bond formation, achieve this objective.

The present invention thus relates to a compound of the formula (I)

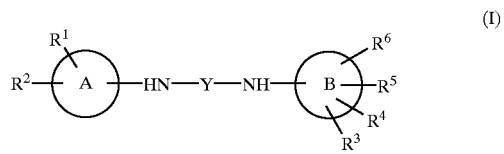

or a salt thereof, where

Y is C=O, C=S, C=NH, (C=O)$_2$ or SO$_2$;

(A) and (B) are each independently an aromatic hydrocarbon group which optionally contains one or more heteroatoms selected from the group consisting of S, O and N, wherein the heteroatom N is optionally substituted with R', and/or the heteroatom S is optionally bonded to =O or (=O)$_2$;

R' is hydrogen, hydroxyalkyl, haloalkyl, aminoalkyl, alkoxy, cyanoalkyl, alkyl or an unsaturated or saturated carbocyclic group selected from the group consisting of cyclopentyl, cyclohexyl, aryl and heteroaryl;

R$^1$ is

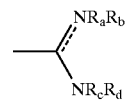

where R$_a$ and R$_c$ are each independently hydrogen, —O—(CO)—R' (where R' is as defined above), hydroxy, hydroxyalkyl, haloalkyl, aminoalkyl, alkoxy, cyanoalkyl, alkyl or an unsaturated or saturated carbocyclic group selected from the group consisting of cyclopentyl, cyclohexyl, aryl, heteroaryl; R$_b$ is an optional substituent which may be independent of $R_a$ and $R_c$ and may be selected from the group as defined above for $R_a$ and $R_c$; $R_d$ is independently hydrogen or one of the following groups:
—(CO)—$R_e$ where $R_e$ is independently hydrogen, alkoxy, alkylthio, halogen, haloalkyl, haloalkyloxy, hydroxyalkyl, hydroxyalkylamino, alkyl, aryl, heteroaryl, amino, aminoalkyl or alkylamino group;
—(CH$_2$)$_n$—$R_f$ where $R_f$ is independently hydrogen, a hydroxy-alkyl, an alkyl, an allyl, an amino, an alkylamino, a morpholino, 2-tetrahydrofuran, N-pyrrolidino, a 3-pyridyl, a phenyl, a benzyl, a biphenyl or another heterocyclic group and n is 0, 1, 2 or 3;
—NR$_a$R$_b$ where $R_a$ and $R_b$ are as defined above;
or $R_a$ forms together with $R_d$ a 5- or 6-membered unsaturated or saturated heterocyclic ring which optionally has 0 to 3 substituents R";
the dotted line means a double bond unless there is a substituent $R_b$ in the formula of $R^1$ as defined above.
R" is independently hydrogen, alkoxy, alkylthio, aminoalkyl halogen, —CO$_2$R', —CR'O, haloalkyl, haloalkyloxy, —NO$_2$, —CN, hydroxyalkyl, alkyl, aryl, heteroaryl, amino, alkylamino or aminoalkyl group or a double bonded oxygen, wherein R' is as defined above;
$R^2$ is a hydrogen, a halogen, alkoxy, alkylthio, —CO$_2$R', —CR'O, haloalkyl, haloalkyloxy, —NO$_2$, —CN, hydroxy, hydroxyalkyl, alkyl, aryl, amino, alkylamino or aminoalkyl group;
$R^3$ is a hydrogen, a halogen, haloalkyl, —NO$_2$, —CN, alkyl or aryl group;
$R^4$ is a hydrogen or a group capable of hydrogen bond formation except for a group as defined for substituent $R^1$;
$R^5$ is hydrogen or, independently of $R^4$, a group selected from the groups as defined above for $R^4$;
$R^6$ is hydrogen or, independently of $R^2$, a group selected from the groups as defined above for $R^2$; and
with the proviso that the compounds of the formula (I) are not compounds in which Y is equal to C=O, both (A) and (B) are a phenyl group and $R^1$ is the group

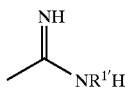

where $R^{1'}$ is hydrogen or phenyl, $R^2$, $R^3$, $R^5$ and $R^6$ are identical and are hydrogen and $R^4$ is phenyl, benzyl, phenoxy, chloro or dimethylamino group in the 3- or 4-position to the NH—Y—NH group of formula (I); and compounds in which (A) and (B) are phenyl and $R^4$, $R^5$ or $R^6$ are in the ortho-position to the NH—Y—NH group of formula (I).

In further embodiments, the invention relates to preparation processes, medicinal and veterinary uses and to pharmaceutical compositions or medicaments and in addition feed additives.

Preferred embodiments of the invention are detailed in the dependent claims, the description and the examples.

For the avoidance of doubt, it is hereby stated that each compound described in the examples is, individually of any other compound, a preferred compound of the invention.

If not stated otherwise, and subject to the same provisos, the compounds of the invention also comprise the salts of the compounds of formula (I).

"(A)" or "(B)" denotes the encircled A or B shown in the formula (I) or the formulae shown further below.

An alkyl group, if not stated otherwise, is preferably a linear or branched chain of 1 to 6 carbon atoms, preferably a methyl, ethyl, propyl, isopropyl, butyl, t-butyl, isobutyl, pentyl or hexyl group, a methyl, ethyl, propyl or isopropyl group being most preferred. The alkyl group in the compounds of formula (I) can optionally be substituted by one or more substituents R, preferably by aryl.

R is independently hydrogen, alkoxy, alkylthio, —CO$_2$R', —CR'O, —NO$_2$, —CN, halogen, haloalkyl, haloalkyloxy, hydroxyalkyl, hydroxyalkylamino, alkyl, aryl, heteroaryl, amino, aminoalkyl or alkylamino group.

An alkoxy group denotes an O-alkyl group, the alkyl group being as defined above.

An alkylthio group denotes an S-alkyl group, the alkyl group being as defined above.

An haloalkyl group denotes an alkyl group which is substituted by one to five preferably three halogen atoms, the alkyl group being as defined above.

A hydroxyalkyl group denotes an HO-alkyl group, the alkyl group being as defined as above.

An haloalkyloxy group denotes an alkoxy group which is substituted by one to five preferably three halogen atoms, the alkyl group being as defined above.

A hydroxyalkylamino group denotes an (HO-alkyl)$_2$—N— group or HO-alkyl-NH—, the alkyl group being as defined above.

An alkylamino group denotes an NH-alkyl or N-dialkyl group, the alkyl group being as defined above.

An aminoalkyl group denotes an NH$_2$-alkyl, monoalkylaminoalkyl, dialkylaminoalkyl group, the alkyl group being as defined above.

A halogen group is chlorine, bromine, fluorine or iodine, fluorine being preferred.

An aryl group preferably denotes an aromatic group having 5 to 15 carbon atoms, in particular a phenyl group. This aryl group can optionally be substituted by one or more substituents R, where R is as defined above, preferably by haloalkyloxy or sulfonamide.

An arylalkyl group denotes an alky group which is substituted by one to three preferably one aryl groups, the alkyl and aryl group being as defined above.

A heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2, 5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzthiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents R, where R is as defined above.

The compounds of the formula (I) according to the invention are disubstituted urea (Y is C=O), guanidine (Y is C=NH), sulphamide (Y is SO$_2$), thiourea (Y is C=S) and oxalamide (Y is (C=O)$_2$) derivatives. The compounds according to the invention are preferably the urea and thiourea derivatives, the urea derivatives being most preferred.

In a preferred embodiment of the invention, (A) is a phenyl group and (B) is an aromatic mono- or bicyclic hydrocarbon group having 5 to 15 carbon atoms, in particular having 5 to 10 carbon atoms, which optionally contains 1–4 N and/or 0 and/or S heteroatoms, in particular by 1 to 3 of these heteroatoms. Preferably, (A) is a phenyl and (B) is selected from a phenyl, furan, thiophene, oxazole, thiazole, isoxazole, isothiazole, 1,2,3-triazole, 1,3,4-thiadiazole, pyran, indole, isoindole, pyridine, pyridazine, pyrimidine, pyrazine, indazole, benzimidazole, triazine, indolizine, benzofuran, benzothiophene, benzothiophene-1,1-dioxide, benzothiazole, purine, quinolizine, quinoline, isoquinoline, cinnoline, phthalazine, quinazoline, naphthyridine and pteridine group. In this connection, any desired combination of these groups can be present for (A) and (B). Particularly preferred compounds are those in which at least (A) or at least (B) is a phenyl group, compounds in which (A) and (B) are each a phenyl group being most preferred.

Preferred compounds are those in which R$^1$ is

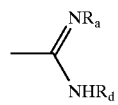

where R$_a$ is hydrogen, —O—(CO)—R' (where R' is as defined above) or hydroxy and R$_d$ is independently hydrogen, —O—(CO)—R' (where R' is as defined above), hydroxy, biphenyl, alkylamino or —(CH$_2$)$_n$—R$_f$ where R$_f$ is an alkylamino or a saturated or unsaturated heterocyclic group and n is 0, 1 or 2; or where R$_a$ and R$_d$ form together a 5- or 6-membered saturated or unsaturated heterocyclic ring which is optionally substituted one or two times by a double bonded oxygen.

Most preferred compounds are those in which R$^1$ is

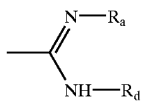

where R$_a$ is hydrogen, —O—(CO)—R' (where R' is as defined above) or hydroxy and R$_d$ is hydrogen, —O—(CO)—R' (where R' is as defined above), hydroxy, 3-pyridyl, alkoxy, —CO$_2$R', alkylamino or —(CH$_2$)$_n$—R$_f$ where R$_f$ is a saturated heterocyclic group or where R$_a$ and R$_d$ form a 5-membered heterocyclic ring which is optionally substituted one or two times by a double bonded oxygen.

The group R$^4$ is hydrogen or a group capable of hydrogen bond formation except for a group defined for substituent R$^1$. A hydrogen bond is formed between a hydrogen atom covalently bond to an electronegative element (proton donor) and a lonely electron pair of an (other) electronegative atom (proton acceptor). R$^4$ can form the hydrogen bond by acting as proton donor or proton acceptor. Preferably, the groups capable of hydrogen bond formation are selected from a halogen, NO$_2$, haloalkyl, haloalkyloxy or CN group or one of the groups mentioned below:

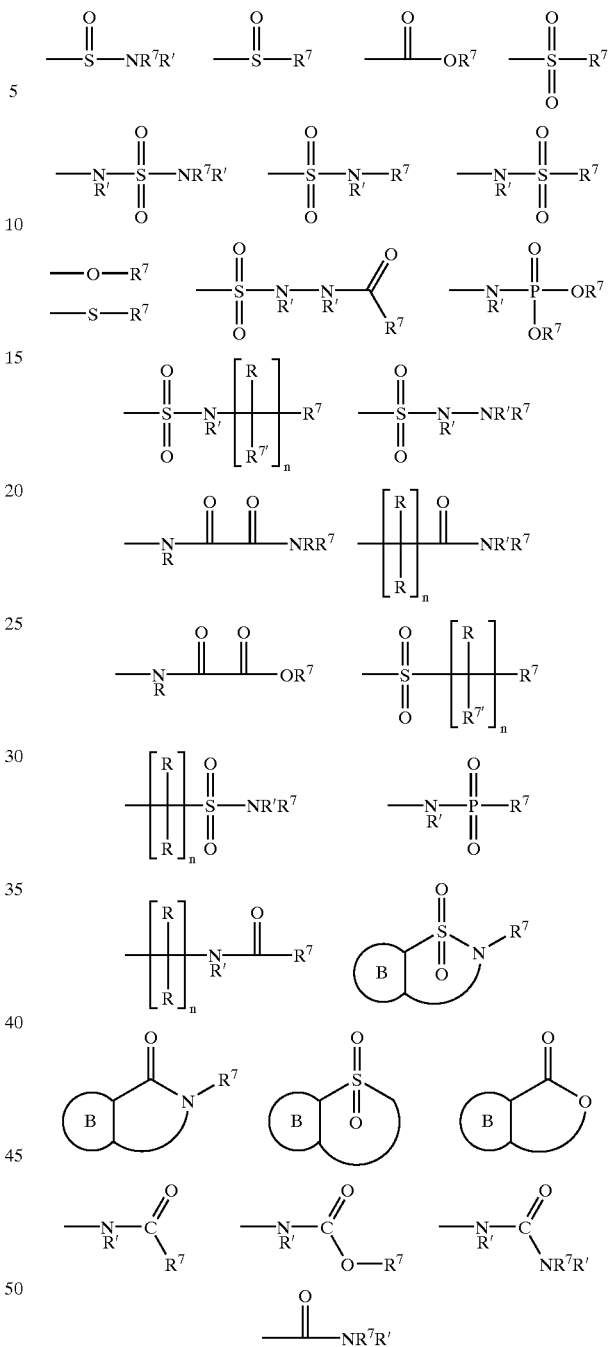

where n is 0, 1, 2 or 3 and where R$^7$ in each case is independently a hydrogen, alkyl, haloalkyl, halogen, nitro adamantyl, hydroxyalkyl, hydroxyalkylamino, aminoalkyl, aryl, biphenyl, or heteroaryl group, which is optionally substituted independently by one or more of the following groups: hydrogen, halogen, alkyl, haloalkyl, amino, aminoalkyl, nitro, alkylamino, hydroxyalkylamino, hydroxy, aryl, heteroaryl, alkoxy, haloalkoxy, COR', CONRR', SO$_2$ NRR', CO$_2$R', where independently R and R' are as defined above. R$^{7'}$ is independently in each case equal to R$^7$, halogen or nitro.

More preferably, $R^4$ is selected from the groups

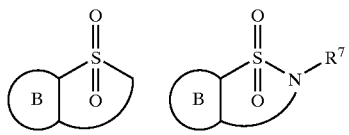

which optionally have 0 to 3 substituents R", where R" is as defined above; and a halogen, $NO_2$, $OCF_3$, $CF_3$, sulfonamide, arylsulfonamide, biarylsulfonamide, amide, alkylsulfonamide, alkylsulfone, arylsulfone, alkylamide, arylamide, benzylamide, alkylthio, and ester group, wherein the aryl and benzyl substituents can again be substituted independently by one or more of the following groups: hydrogen, halogen, alkyl, haloalkyl, haloalkyloxy, aryl, amino, aminoalkyl, nitro, alkylamino, hydroxy, alkoxy, CONRR', hydroxyalkylsulfonamide, $SO_2NRR'$, $CO_2R'$, aminoalkylsulfonamide, (hydroxyalkyl)$_2$sulfonamide and (aminoalkyl)$_2$sulfonamide, wherein R and R' independently are as defined before.

Most preferably $R^4$ is a bisarylsulfonamide or a substituted benzylsulfonamide where the substituents are independently one or more of the following groups: hydrogen, halogen, haloalkyl, haloalkoxy, CONRR', $SO_2NRR'$ and $CO_2R'$, where R and R' independently are as defined above.

$R^2$, $R^3$, $R^5$ are preferably hydrogen.

$R^6$ is preferably hydrogen, a halogen, nitro, hydroxy, $OCH_3$, $CF_3$ or $OCF_3$ group.

n is preferably 0 or 1 or 2.

The substituents $R^1$, $R^4$ and/or $R^5$ in monocyclic groups of (A) and (B) are preferably present in the 3- or 4-position to the NH—Y—NH group of the compound of the formula (I). If (A) and/or (B) is a bicyclic group, $R^1$, $R^4$ and/or $R^5$ are preferably present in the 1- to 4-position, in particular in the 3-position. The further substituents $R^2$, $R^3$ and $R^6$ are preferably present in the 2- or 3-position, in each case relative to the NH—Y—NH group of the compound of formula (I). If (B) is a phenyl group $R^4$, $R^5$ and/or $R^6$ is not in the 2- or 6-position to the NH—Y—NH-group of the compound of the formula (I).

Particularly preferred compounds of the formula (I) are the urea derivatives (i.e. Y is C=O), in which (A) and (B) in most cases are a phenyl group but (B) also can be benzothiophene-1,1-dioxid, $R^1$ is an optionally substituted or cyclic amidine group, $R^4$ is a group capable of hydrogen bond formation, in particular a $CF_3$, $OCF_3$, sulfonamide, benzylsulfonamide, arylsulfonamide or arylsulfone group, optionally substituted preferably by halogen, $OCF_3$ or sulfonamide and $R^2$, $R^3$, $R^5$ and $R^6$ are in each case hydrogen.

The salts of the compounds of formula (I) include phosphates, nitrates, hydrochlorides, hydrobromides, perchlorates, sulphates, citrates, lactates, tartrates, isethionates, maleates, fumarates, mandelates, benzoates, ascorbates, cinnamates, benzenesulfonates, methanesulfonates, stearates, succinates, glutamates, glycolates, toluene-4-sulfonates, formates, malonates, naphthalene-2-sulfonates, salicylates and acetates. These can be formed via well-known processes. Further suitable salts are all other salts customary in the pharmaceutical recipe, for example such as are described in *International Journal of Pharmaceutics*, 33 (1986) 201–217. The hydrochlorides are most preferred.

The compounds of the formula (I) according to the invention can be prepared according to the methods customary to the person skilled in the art or processes known from the literature. For example, these compounds can be prepared in liquid phase or via a solid-phase technique.

To prepare the urea derivatives, all methods known for the preparation of ureas can be employed. In the solid phase, for example, the methods which are described in *Organic Synthesis on Solid Phase*, Ed. F. Z. Dörwald, p. 331 ff, Wiley-VCH, Weinheim, 1999 can be applied. For the preparation of urea derivatives, suitable liquid-phase processes are described, for example, in Houben-Weyl, vol. E4, *Kohlensäure-Derivate* [*Carboxylic acid derivatives*] Publisher Hagemann, Georg Thieme Verlag, Stuttgart, 1983. Thus, in the liquid-phase technique a compound of the formula (I) in which $R^4$ is a group capable of hydrogen bond formation and $R^1$ is an amidine group can be prepared by reacting a suitable aniline which contains the group of $R^4$ capable of hydrogen bond formation with a suitable isocyanate which contains a nitrile group or another group convertible to the amidine group, which can be present in protected or unprotected form. The nitrile group or the group convertible to the amidine group is then converted into the amidine group via known processes. Alternatively, the aniline containing the group capable of hydrogen bond formation can be converted into an isocyanate and this can be converted to an urea via known methods using a suitable aniline which contains a nitrile group or another group convertible into amidine, for this compare *The Chemistry of Amidines and Imidates*, Ed. Saul Patai, John Wiley & Sons, 1975. Furthermore, an amidine group protected by a protective group (suitable protective groups for this are described, for example, in *Nitrogen Protecting Groups: Recent Developments and New Applications*, G. Theodoridis, Tetrahedron 56 (2000), 2339–2358) can be converted into an isocyanate and reacted with an aniline containing the group capable of hydrogen bond formation. Compounds of this type lead, after the removal of the protective group, to the amidine-substituted urea. Anilines which contain an amidine or other basic functions can be converted directly into ureas according to processes known in the literature. In this connection, reagents can also be employed which include a latently activated carbonate unit which reacts with anilines under suitable conditions to give ureas. Examples of such reagents are carbonyldiimidazole or other reagents mentioned in *Advanced Organic Chemistry*, J. March, p. 396, John Wiley & Sons, New York, 1992. Processes suitable for the preparation of the urea derivatives are also described in DE-A-2 334 355, DE-A-2 928 485 and WO 9639382.

In a particularly preferred embodiment, the invention relates to a process for the preparation of the compounds according to the invention wherein the process is characterized in that a compound of the formula (III)

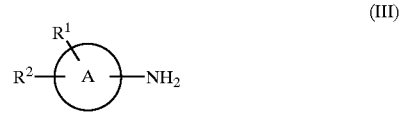

where (A), $R^1$ and $R^2$ are as defined above is reacted with an isocyanate of the formula (V)

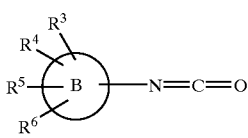

(V)

where (B), $R^3$, $R^4$, $R^5$ and $R^6$ are as defined above.

Preferably, this process is carried out in the liquid phase. The compounds of the formula (I) can also be prepared by solid phase techniques, where the compound of the formula (III) is optionally bonded to a solid support via the $NH_2$ group of $R^1$. All groups (A), (B), $R^1$, $R^2$, $R^4$, $R^5$ and $R^6$ are defined in greater detail as described above under the compound of the formula (I) according to the invention.

For example, compounds of the formula (I) where $R^1$ is an amidine group can be prepared by the solid phase method. Therefore a suitable aromatic amidine is first linked to a polystyrene resin via a urethane function, for example by reaction of nitrobenzamidine in dimethylacetamide (DMA) in the presence of diisopropylethylamide (DIEA) with a nitrophenyl-carbonate Wang-resin (D. M. Dixit, et al. (1978) Israel J. Chem., 17, 248; B. A. Dressman, et al. (1996) Tetrahedron Lett., 37, 937), for this also see Solid Phase Synthesis of N-substituted amidinophenoxy pyridines as Factor $X_a$ Inhibitors, Raju Mohan et al., Bioorg. Med. Chem. Lett. 8 (1998), 1877–1882. Afterwards, the nitro group is converted into an amino group by reduction using tin(II) chloride monohydrate, compare *Organic Synthesis on Solid Phase*, Ed. F. Z. Dörwald, p. 247, Wiley-VCH, Weinheim, 1999.

The resin-bonded aminobenzamidine obtained in this manner can be reacted with an isocyanate having the substituents $R^3$, $R^4$, $R^5$ and $R^6$ as defined above. The final compound is obtained by removal of the compound obtained from the resin by means of trifluoro-acetic acid (TFA; 30–50% strength) in dichloromethane (DCM).

Compounds according to the invention where $R^4$ is a sulfonamide, alkylsulfonamide, arylalkylsulfonamide or arylsulfonamide group can be obtained by a solution or solid phase method. In the solid phase method, the compounds of formula (I) can be prepared by reaction of the resin-bonded aminobenzamidine mentioned beforehand with chlorosulfonylisocyanate, subsequent conversion of the resulting chlorosulfonylurea to the sulfonamide by warming in the presence of an appropriate amine and DIEA in DMA and subsequent removal of the resin support with TFA. In the solution method, the compounds of formula (I) can be obtained by reaction of a sulfonamide with the appropriate isocyanatobenzonitrile.

The sulfonamides can be obtained by the reaction of nitrobenzenesulfonylchloride with the appropriate amine and subsequent reduction of the nitro group or the reaction of acetamidobenzenesulfonylchloride with the appropriate amine and subsequent saponification of the acetamido group.

Another direct method to synthesize compounds according to the invention where $R^4$ is a sulfonamide, alkylsulfonamide or arylsulfonamide group can be prepared by reaction of aminobenzonitrile with chlorosulfonylisocyanate and subsequent conversion of the resulting chlorosulfonylurea with the appropriate amine according to Scheme 1.

Conversion of the nitrile to the amidine is achieved by the Pinner-reaction. Substituted amidines are obtained by reacting the nitrile or iminoether with the appropriate amine according to Scheme 1 and mentioned in J. Med. Chem., 1996, 39, 4935–4941; Heterocycles, 1986, 24 (5), 1377–1380; Bioorg. Med. Chem., 2001, 9, 585–592; Synthetic Commun., 1998, 28 (23), 4419–29; Eur. J. Org. Chem., 1998, 853–859 or J. Med. Chem., 1992, 35, 4393–4407. In case of acid labile groups present the nitrile is first converted to the amidoxime, which was reduced in the presence of zinc powder to the amidine after O-acylation with acetic acid anhydride as described in the European patent application EP 0990646.

Scheme 1:

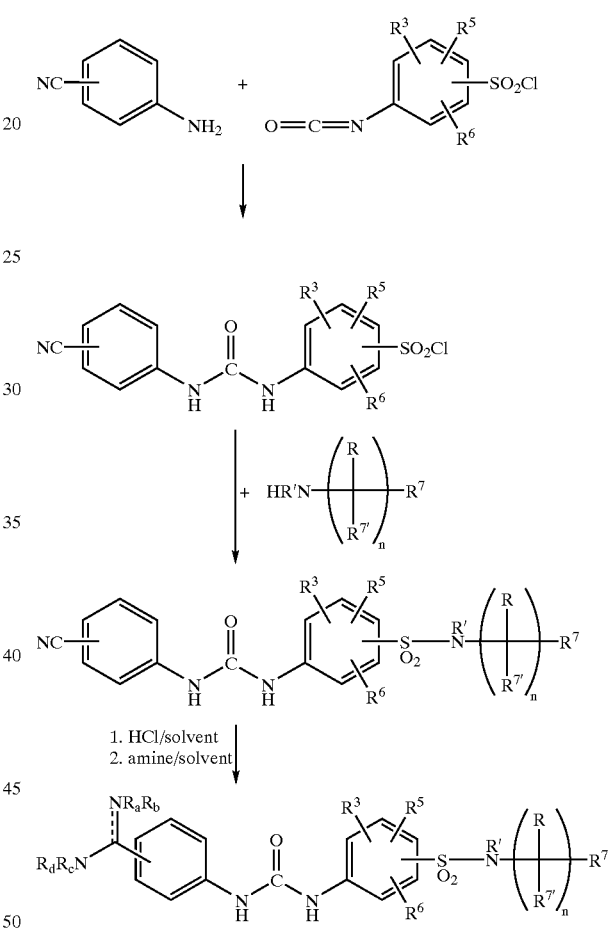

1. HCl/solvent
2. amine/solvent

The invention also relates to a process for the preparation of compounds of the formula (I), in which Y is equal to C=O, C=S, C=NH or $SO_2$, where the process is characterized in that a compound of the formula (II)

(II)

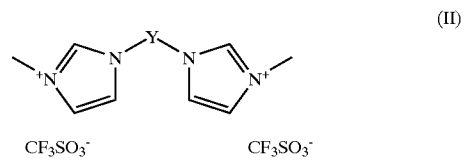

$CF_3SO_3^-$  $CF_3SO_3^-$ is reacted both with a compound of the formula (III)

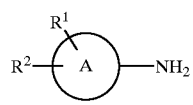

(III)

where (A), $R^1$ and $R^2$ are as defined above and with a compound of the formula (IV)

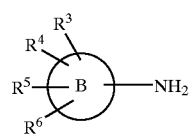

(IV)

where (B), $R^3$, $R^4$, $R^5$ and $R^6$ are as defined above.

The reagent 1,1'-carbonylbis(3-methylimidazolium) triflate (CBMIT; the triflate radical designates the trifluoromethane-sulfonyl radical) is used, which is described in 1,1'-car-bonylbis(3-methylimidazolium) triflate: *An efficient Reagent for Aminoacylations*, A. K. Saha et al., J. Am. Chem. Soc. 1989, 111, 4856–4859). This reagent enables, under mild conditions, the preparation of compounds of the formula (I), in which Y is equal to C=O, C=S, C=NH or SO$_2$. The reaction with this reagent can be carried out either in the liquid phase or on solid phase, the preparation in the liquid phase being preferred. All groups (A), (B), $R^1$, $R^2$, $R^4$, $R^5$ and $R^6$ are defined in greater detail as described above under the compound of the formula (I) according to the invention.

In literature, CBMIT has been used to make amides (Ashis K. Saha, et al. JACS 1998, 11, 4856–4859) and asymmetric ureas (Robert A. Batey, Tetrahedron Letters 39 (1998) 6267–6270).

Thiourea derivatives can also be made by other methods as conversion of ureas to thioureas by Lawesson reagent or P$_2$S$_5$ (Bull. Soc. Chim., Belg. Synth. 1978, 87, 229–238 or Org. Synth., 1984, 62, 158–164 or Chem. Rev., 1961, 61, 45–86.) Other methods to make thioureas are described in J. Comb. Chem., 2000, 2, 75–79 or in Houben-Weyl, Vol. E4, Kohlensäure-Derivate [Carbonic acid derivatives], Editor Hagemann, Georg Thieme Verlag, Stuttgart, 1983, 484–505.

Bisarylsulphamides can also be prepared by other methods as described in Tetrahedron Letters, 1997, Vol. 38, 8691–8694 or in WO 01/36383.

Bisaryloxalamides can also be prepared by using oxalic acid ester (preferably hexafluoroisopropylester) or oxalylchloride instead of CBMIT. These methods are described in J. Org. Chem., 1997, 62, 5908–5919 or in U.S. Pat. Nos. 3,529,982, 4,003,875, and in EP 0507732.

Therefore the compounds according to the invention and medicaments prepared therewith are generally useful for the treatment of diseases where the inhibition of intracellular protein degradation pathways preferably the proteasome pathway is of benefit. (Cancer Research, 1999, Vol. 59, 2615–2622; Invest. New Drugs, 2000, Vol. 18, 109–121; Ashley Pub., 1999, 1397–1406) The present invention is directed toward the use of molecules that target proteases, especially prokaryotic, eukaryotic or viral proteases or proteasome to modulate cellular pathways or to effect cytoprotection. The cellular pathways are selected from the group consisting of those that regulate cell activation, cell proliferation, cell survival, cell differentiation, cell cycle, cell maturation and cell death or to induce systemic changes in metabolism such as changes in sugar, lipid or protein metabolism. Protease inhibitors can be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis. The compounds according to the invention and medicaments prepared therewith are generally useful for the treatment of cell proliferation disorders, for the treatment or prophylaxis of immunological diseases and conditions (as for instance inflammatory diseases, neuroimmunological diseases, autoimmune diseases or other) infectious diseases such as Lyme disease, herpes, hepatitis, other chronic infections such as those induced by other viruses as HIV, bacteria and fungi. These diseases and conditions include but are not limited to cancer as hematological (e.g. leukemia, lymphoma, myeloma) or solid tumors (for example breast, prostate, liver, bladder, lung, esophageal, stomach, skin, pancreatic, brain, uterine, colon, head and neck, and ovarian, melanoma, basal and squameous cell carcinoma, sarcomas as Kaposi's sarcoma and osteosarcoma), cardiovascular diseases as myocarditis, arterial stenosis as restenosis following angioplasty, ischemia and reperfusion injury as in stroke, heart attack or others, renal diseases such as polycystic kidney disease or glomerulonephritis, gout, allergic disorder, asthma, acute and delayed hypersensitivity, graft-versus-host or host-versus-graft disease, transplant rejection, multiple sclerosis, Alzheimers' disease, Parkinsons' disease, Huntington disease and acute disseminated encephalomyelitis, treatment of disorders involving T-cells such as aplastic anemia and DiGeorge syndrome, Graves' disease, lupus erythematosus, Sjogren's Syndrome, all forms of rheumatism or arthritis as rheumatoid arthritis, ulcerative colitis, inflammatory bowel disease, Morbus Crohn, as well as other chronic inflammations, chronic diarrhea, insulin dependent diabetes mellitus and non-insulin dependent diabetes and other metabolic diseases, dermatological disorders such as psoriasis, abnormal wound healing, burn, keloid, scleroderma, keratinization disorders or others, airway diseases induced by an irritant, conditions associated with aging, ARDS, ITP, sepsis and septic shock, trauma and similar disorders or other diseases that can be treated by the modulation of intracellular protein degradation pathways (e.g. ubiquitin or proteasome dependent pathways) as well as pathologic conditions that can be the consequences of these diseases.

The present invention also relates to the use of a compound of the formula (I)

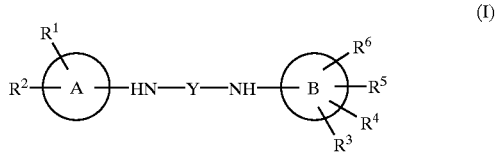

(I)

or a salt thereof, where
Y is C=O, C=S, C=NH, (C=O)$_2$ or SO$_2$;
(A) and (B) are each independently an aromatic hydrocarbon group which optionally contains one or more heteroatoms selected from the group consisting of S, O and N, wherein the heteroatom N is optionally substituted with R' and/or the heteroatom S is optionally bonded to =O or (=O)$_2$;

R' is hydrogen, hydroxyalkyl, haloalkyl, aminoalkyl, alkoxy, cyanoalkyl, alkyl or an unsaturated or saturated carbocyclic group selected from the group consisting of cyclopentyl, cyclohexyl, aryl and heteroaryl;

$R^1$ is

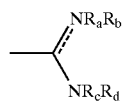

where $R_a$ and $R_c$ are each independently hydrogen, —O—(CO)—R' (where R' is as defined above), hydroxy, hydroxyalkyl, haloalkyl, aminoalkyl, alkoxy, cyanoalkyl, alkyl or an unsaturated or saturated carbocyclic group selected from the group consisting of cyclopentyl, cyclohexyl, aryl, heteroaryl; $R_b$ is an optional substituent which may be independently of $R_a$ and $R_c$ and may be selected from the group as defined above for $R_a$ and $R_c$; $R_d$ is hydrogen or one of the following groups:

—(CO)—$R_e$ where $R_e$ is independently hydrogen, alkoxy, alkylthio, halogen, haloalkyl, haloalkyloxy, hydroxyalkyl, hydroxyalkylamino, alkyl, aryl, heteroaryl, amino, aminoalkyl or alkylamino group;

—(CH$_2$)$_n$—$R_f$ where $R_f$ is independently hydrogen, a hydroxy-alkyl, an alkyl, an allyl, an amino, an alkylamino, a morpholino, 2-tetrahydrofuran, N-pyrrolidino, a 3-pyridyl, a phenyl, a benzyl, a biphenyl or another heterocyclic group and n is 0, 1, 2 or 3;

—$NR_aR_b$ where $R_a$ and $R_b$ are defined above;

or $R_a$ forms together with $R_d$ a 5- or 6-membered unsaturated or saturated heterocyclic ring which optionally has 0 to 3 substituents R";

the dotted line means a double bond unless there is a substituent $R_b$ in the formula of $R^1$ as defined above.

R" is independently hydrogen, alkoxy, alkylthio, aminoalkyl halogen, —CO$_2$R', —CR'O, haloalkyl, haloalkyloxy, —NO$_2$, —CN, hydroxyalkyl, alkyl, aryl, heteroaryl, amino, alkylamino or aminoalkyl group or a double bonded oxygen, wherein R' is as defined above;

$R^2$ is a hydrogen, a halogen, alkoxy, alkylthio, —CO$_2$R', —CR'O, haloalkyl, haloalkyloxy, —NO$_2$, —CN, hydroxy, hydroxyalkyl, alkyl, aryl, amino, alkylamino or aminoalkyl group;

$R^3$ is a hydrogen, a halogen, haloalkyl, —NO$_2$, —CN, alkyl or aryl group;

$R^4$ is a hydrogen or a group capable of hydrogen bond formation except for a group as defined for substituent $R^1$;

$R^5$ is hydrogen or, independently of $R^4$, a group selected from the groups as defined above for $R^4$;

$R^6$ is hydrogen or, independently of $R^2$, a group selected from the groups as defined above for $R^2$;

preferably with the proviso that the compounds of the formula (I) are not compounds in which Y is equal to C=O, both (A) and (B) are a phenyl group, $R^1$ is the group

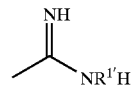

where $R^{1'}$ is hydrogen or phenyl, $R^2$, $R^3$, $R^5$ and $R^6$ are identical and are hydrogen and $R^4$ is phenyl, benzyl, phenoxy, chloro or dimethylamino group in the 3- or 4-position to the NH—Y—NH group of formula (I), most preferred with the compounds of the formula (I) are not compounds in which Y is equal to C=O, both (A) and (B) are a phenyl group,and $R^1$ is the group

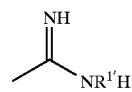

where $R^{1'}$ is hydrogen or phenyl, $R^2$, $R^3$, $R^5$, and $R^6$ are identical and are hydrogen and $R^4$ is phenyl, benzyl, phenoxy, chloro or a dimethylamino group in the 3- or 4-position to the NH—Y—NH group of formula (I);

and compounds in which (A) and (B) are phenyl and $R^4$, $R^5$ or $R^6$ are in the ortho-position to the NH—Y—NH group of formula (I) for the preparation of a medicament for the inhibition of the intracellular protein-degradation pathway, preferably, for the preparation of a medicament for the treatment of diseases which are used or relieved by the inhibition of the proteasome pathway, most preferably for the preparation of a medicament for the treatment of diseases which are used or relieved by the inhibition of the chymotryptic activity of the multicatalytic proteasome complex.

The compounds used according to the invention can be administered orally, parenterally (e.g. intravenously, intraperitoneally, intramusculary, subcutaneously, rectaly or vaginaly), topically or by inhalation, oral administration being preferred. In this case, the compounds are used alone as mono substances or in combination with other therapies or active compounds, for example with medicaments already known for the treatment of diseases, where the inhibition of the intracellular protein degradation pathway especially the proteasome pathway is of benefit, where in the latter case a favourable, additively reinforcing action can be observed. For example in cancer treatment the compounds can be used in adjunction to radiation, established or experimental chemotherapy. In particular, such modulation of cellular pathways or systemic metabolism using a protease inhibitor will be utilized to effect human or animal therapy. Amounts suitable for administration are 0.01 to 20 mg/kg day preferably 0.1 to 5 mg/kg day in humans or animals. The protease inhibitors of the invention may be administered to a human or other animal in an amount sufficient to produce a therapeutic, prophylactic, cosmetic or dermatological effect. The present invention therefore also relates to a pharmaceutical composition which contains at least the compound according to the invention. In addition, the pharmaceutical composition can contain further customary, as a rule inert, vehicles or excipients.

The compounds according to the invention and medicaments prepared therewith are also suitable for the treatment of diseases which occur due to attack of humans or animals by protozoa. Veterinary- and human-pathogenic protozoa of this type are preferably parasites of the phyla Apicomplexa and Sarcomastigophora, in particular trypanosomes, plasmodia (malarial parasites), toxoplasma, leishmania, babesia and theileria, cryptosporidiidae, sarcocystidae, eimeria and isospora, amoebae and trichomonads. The compounds or corresponding medicaments are particularly preferably suitable for the treatment of diseases caused by plasmodia, in particular for the treatment of tropical malaria, which is caused by *Plasmodium falciparum*, for the treatment of benign tertian malaria, caused by *Plasmodium vivax* and *Plasmodium ovale* and for the treatment of quartan malaria, caused by *Plasmodium malariae*; they are moreover suitable for the treatment of toxoplasmosis, caused by *Toxoplasma gondii*, of coccidiosis, caused by *Isospora belli*, of intestinal sarcosporidiosis, caused by *Sarcocystis suihominis*, of cryptosporidiosis, caused by *Cryptosporidium parvum*, of the African sleeping sickness caused by *Trypanosoma brucei rhodesiense* and *Trypanosoma brucei gambiense*, of Chagas' disease, which is caused by *Trypanosoma cruzi*, the cutaneous and visceral and also other forms of leishmaniosis caused by various *leishmania* species, and also for the treatment of animals which have been infected by veterinary pathogenic protozoa, such as by *Theileria parva*, the parasite of east-coast fever of cattle, *Typanosoma congolense congolense*, *Trypanosoma vivax vivax* and *Trypanosoma brucei brucei*, parasites causing *Nagana cattle* disease, *Babesia begemina*, the parasite of Texas fever in cattle and buffalo, *Babesia bovis*, the parasite of european bovine babesiosis, and babesioses in dogs, cats and sheep, sarcocystidae, the parasites of sarcocystosis in sheep, cattle and pigs, cryptosporidiidae, the parasites of cryptosporidiosis in cattle and birds, coccidia, the parasites of coccidioses of rabbits, cattle, sheep, goats and pigs, but in particular of chicken and turkey hens as for example *Eimeria tenella*. Most preferred is the use of the compounds according to the invention for the treatment of coccidiosis or malarial diseases or for the production of a medicament or, if appropriate, of a feed for the treatment of coccidioses or malarial diseases. The treatment can in this case be carried out prophylactically or curatively.

The present invention also relates to the use of a compound of the formula (I)

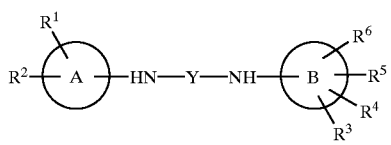

(I)

or a salt thereof, where

Y is C=O, C=S, C=NH, (C=O)$_2$ or SO$_2$;

(A) and (B) are each independently an aromatic hydrocarbon group which optionally contains one or more heteroatoms selected from the group consisting of S, O and N, wherein the heteroatom N is optionally substituted with R' and/or the heteroatom S is optionally bonded to =O or (=O)$_2$;

R' is hydrogen, hydroxyalkyl, haloalkyl, aminoalkyl, alkoxy, cyanoalkyl, alkyl or an unsaturated or saturated carbocyclic group selected from the group consisting of cyclopentyl, cyclohexyl, aryl and heteroaryl;

R$^1$ is

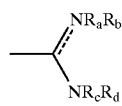

where R$_a$ and R$_c$ are each independently hydrogen, —O—(CO)—R' (where R' is as defined above), hydroxy, hydroxyalkyl, haloalkyl, aminoalkyl, alkoxy, cyanoalkyl, alkyl or an unsaturated or saturated carbocyclic group selected from the group consisting of cyclopentyl, cyclohexyl, aryl, heteroaryl; R$_b$ is an optional substituent which may be independently of R$_a$ and R$_c$ and may be selected from the group as defined above for R$_a$ and R$_c$; R$_d$ is hydrogen or one of the following groups:

—(CO)—R$_e$ where R$_e$ is independently hydrogen, alkoxy, alkylthio, halogen, haloalkyl, haloalkyloxy, hydroxyalkyl, hydroxyalkylamino, alkyl, aryl, heteroaryl, amino, aminoalkyl or alkylamino group;

—(CH$_2$)$_n$—R$_f$ where R$_f$ is independently hydrogen, a hydroxy-alkyl, an alkyl, an allyl, an amino, an alkylamino, a morpholino, 2-tetrahydrofuran, N-pyrrolidino, a 3-pyridyl, a phenyl, a benzyl, a biphenyl or another heterocyclic group and n is 0, 1, 2 or 3;

—NR$_a$R$_b$ where R$_a$ and R$_b$ are defined above;

or R$_a$ forms together with R$_d$ a 5- or 6-membered unsaturated or saturated heterocyclic ring which optionally has 0 to 3 substituents R";

the dotted line means a double bond unless there is a substituent R$_b$ in the formula of R$^1$ as defined above;

R" is independently hydrogen, alkoxy, alkylthio, aminoalkyl halogen, —CO$_2$R', —CR'O, haloalkyl, haloalkyloxy, —NO$_2$, —CN, hydroxyalkyl, alkyl, aryl, heteroaryl, amino, alkylamino or aminoalkyl group or a double bonded oxygen, wherein R' is as defined above;

R$^2$ is a hydrogen, a halogen, alkoxy, alkylthio, —CO$_2$R', —CR'O, haloalkyl, haloalkyloxy, —NO$_2$, —CN, hydroxy, hydroxyalkyl, alkyl, aryl, amino, alkylamino or aminoalkyl group;

R$^3$ is a hydrogen, a halogen, haloalkyl, —NO$_2$, —CN, alkyl or aryl group;

R$^4$ is a hydrogen or a group capable of hydrogen bond formation except for a group as defined for substituent R$^1$;

R$^5$ is hydrogen or, independently of R$^4$, a group selected from the groups as defined above for R$^4$;

R$^6$ is hydrogen or, independently of R$^2$, a group selected from the groups as defined above for R$^2$; and with the provisio that compounds in which (A) and (B) ar phenyl and R$^4$, R$^5$ and R$^6$ are in the ortho-position to the NH—Y—NH group of formula (I), preferably with the proviso that the compounds of the formula (I) are not compounds in which Y is equal to C=O, both (A) and (B) are a phenyl group, R$^1$ is the group

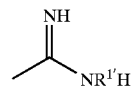

where R$^{1'}$ is hydrogen or phenyl, R$^2$, R$^3$, R$^5$ and R$^6$ are identical and are hydrogen and R$^4$ is phenyl, benzyl, phenoxy, chloro or dimethylamino group in the 3- or 4-position to the NH—Y—NH group of formula (I); and compounds in which (A) and (B) are phenyl and R$^4$, R$^5$ or R$^6$ are in the ortho-position to the NH—Y—NH group of formula (I) for the preparation of a medicament for the treatment of diseases caused by protozoa, preferably for the treatment of malaria diseases, coccidosis, trypanosomiasis, such as African sleeping sickness or chargas disease, and/or leishmaniasis.

The compounds used according to the invention can be administered orally or parenterally (e.g. intravenously, intraperitoneally or intramusculary), oral administration being preferred. In this case, the compounds are used alone as monosubstances or in combination with other active compounds, for example with medicaments already known for the treatment of diseases caused by protozoa, where in the latter case a favourable, additively reinforcing action can be observed. Amounts suitable for administration are 1 to 1000 mg/day in humans or animals. The present invention therefore also relates to a pharmaceutical composition which contains at least the compound according to the invention. In addition, the pharmaceutical composition can contain further customary, as a rule inert, vehicles or excipients.

The invention moreover relates to a feed additive which contains at least the compound according to the invention. Customary feed mixtures, for example, in particular those for poultry or agricultural animals, can be admixed to this feed additive. When used as a feed additive, the amount of the compound according to the invention is 20 to 750 ppm, preferably 2 to 200 mg/kg.

The invention thus makes available novel medicaments for the treatment of the various forms of malaria, in particular for the treatment of tropical malaria. It was surprising that the compounds proved active not only against chloroquine-sensitive, but also against chloroquine-resistant, Plasmodium falciparum strains. In addition to the hitherto customary treatment of the later erythrocytic stage of the malarial parasite, with these compounds the treatment of the early form of malaria by destruction of the parasites even in the liver also appears to be very particularly advantageous with these compounds.

The compounds used according to the invention can also be employed in the form of a precursor (prodrug) or in appropriately modified form which releases the active compound in vivo or under physiological conditions. Precursors of this type can be obtained, for example, by masking the amidine group by a hydroxy or —O—(CO)—R' group, wherein R' is as defined above (e.g. according to WO 95/01168) or by any other method as described in the literature, e.g. J. Med. Chem. 43, No. 19, p. 3461 (2000).

The invention is illustrated in greater detail with the aid of the following examples, which are preferred embodiments of the invention and do not restrict the scope of the invention.

EXAMPLES

Abbreviations Index

The following abbreviations are presently used:
DMA=dimethylacetamide; DCM=dichloromethane; DMF=dimethylformamide; DIEA=diisopropylethylamide; EDTA=ethylenediamintetraacetate disodium salt; SDS=sodiumdodecylsulfate; Hepes=2-[4-(2-Hydroxyethyl)-1-piperazinyl)-ethansulfonsaure; AMC=7-Amino-4-methylcoumarin; TFA=trifluoroacetic acid; CBMIT=1,1'-carbonylbis(3-methyl-imidazolium) triflate; eq=eqivalents; rt=room temperature; min=minutes; h=hours; d=day; HPLC-MS=high-performance liquid chromatography-mass spectrometry.

Reagents Used

Wang-resin (200–400 mesh) with a functional loading of 1.1 mmol/g was obtained from Calbiochem-Novabiochem, Postfach 1167, D-65796 Bad Soden.

Preparation Process

The compounds described in the following table were prepared according to one or more of the following synthesis methods 1 to 9. The compounds prepared were then investigated for their antimalarial activity.

Analytical Determination

In the following the mass found by mass spectrometry, the exact molecular mass, the NMR-data at 300 MHz (abbreviations: br.=broad, s=singlet, d=doublet, t=triplet, q=quartet, m=multiplet, J=$^1$H—$^1$H coupling constant).

Synthesis Method 1

Wang-resin was suspended in dry DMA, p-nitrophenylchloroformate (1.2 eq) and DIEA (1.2 eq) were added and the mixture was kept on a shaker for 12 h. The resin was collected by filtration and washed several times with isopropanol and DCM. The resin was then suspended again in DMA and 3-nitro-phenylbenzamidine (1.5 eq) and DIEA (1.5 eq) were added and the mixture was kept on a shaker overnight and then washed with isopropanol and DCM. A solution of $SnCl_2.H_2O$ (1M) in DCM/DMF (1/1) was then added and the mixture was shaken for a further 5 h.

Finally, the resin was washed again with isopropanol and DCM and then dried. This resin was then used for the synthesis methods 2, 2a, 2b, 3, 5 and 6.

Synthesis Method 2

An aliquot (100 mg) of the resin modified according to synthesis method 1 was suspended in dry DCM and 5 eq of the appropriate isocyanate were added. The mixture was kept in a suitable vessel overnight on a shaker. The resin was collected by filtration and washed successively with DCM, isopropanol and DCM. The resin was then treated with 50% strength TFA in DCM for 1 h, filtered and the filtrate was concentrated in vacuo. The crude urea was first analysed by HPLC-MS and then purified by preparative HPLC.

Synthesis Method 2a

An aliquot (100 mg) of the resin modified according to synthesis method 1 was suspended in dry DCM and 5 eq nitrophenylisocyanate were added. The mixture was kept in a suitable vessel overnight on a shaker. The resin was collected by filtration and washed successively with DCM, isopropanol and DCM. A solution of $SnCl_2.H_2O$ (1 M) in DCM/DMF (1/1) was then added and the mixture was shaken for a further 5 h. Finally, the resin was washed again with isopropanol and DCM and then dried. The so obtained resin was treated with DIEA (2 eq) and the appropriate acide chloride (2 eq). The resin was collected by filtration and washed successively with DCM, isopropanol and DCM. The resin was then treated with 50% strength TFA in DCM for 1 h, filtered and the filtrate was concentrated in vacuo. The crude urea was first analysed by HPLC-MS and then purified by preparative HPLC.

Synthesis Method 3

The modified resin prepared according to synthesis method 1 was reacted overnight at rt in dry DCM with chlorosulfonyl-isocyanate (1.5 eq). The resin was collected by filtration, washed with DCM and dried. A small aliquot of the resin (100 mg) was reacted at 80° C. for 3 h with the appropriate amine and DIEA in DMA. The resin was collected by filtration, washed with isopropanol and DCM and then treated with 50% strength TFA for 1 h. The TFA solution was collected by filtration, concentrated in vacuo and analysed by analytical HPLC-MS. The crude product was purified by preparative HPLC.

Synthesis Method 4

1,1-carbonyldiimidazole (1 eq) was dissolved in 5 ml nitromethane. The solution was cooled to 4° C. and methyltriflate (2 eq) were added dropwise. The reaction was stirred for 30 min at 4° C., then the appropriate aniline or sulfonamide dissolved in 2 ml DMA was added dropwise. The reaction was stirred for 2.5 h at rt, then aminobenzamidinedihydro-chlorid dissolved in 1 ml DMA containing DIEA (1 eq) was added. After stirring overnight at rt the solvent was evaporated and the product purified by flash chromatography on silica gel using a gradient of AcOEt-MeOH from 5% to 55% MeOH or by preparative HPLC.

Synthesis Method 4a

Analog to method 4 only that 1,1-thiocarbonyldiimidazole (1 eq) was used instead of 1,1-carbonyldiimidazole.

Synthesis of 3-[3-(4-benzylsulfamoyl-phenyl)-thioureido]-benzamidine (90)

1,1-Thiocarbonyldiimidazole (142.5 mg, 0.8 mmol) was dissolved in nitromethane (5 ml). The solution was cooled to 4° C. and methyltriflate (0.181 ml, 1.6 mmol) was added dropwise. The reaction was stirred for 30 min at 4° C., then 4-amino-N-benzylbenzenesulfonamide (210 mg, 0.8 mmol), dissolved in DMA (2 ml), was added dropwise. The reaction was stirred for 2.5 h at rt, then 3-aminobenzamidine dihydrochloride (166.5 mg, 0.8 mmol) and DIEA (0.140 ml, 0.8 mmol) dissolved in DMA (1 ml) were added. After stirring 16 h at rt the solvent was evaporated. After purification by flash chromatography (A:AcOEt, B:MeOH, 95% to 45% of A in 28 min) the product was obtained with a 15% yield.

Synthesis Method 4b

Analog to method 4 only that 1,1-sulfonyldiimidazole (1 eq) was used instead of 1,1-carbonyldiimidazole.

Synthesis Method 5

An aliquot (100 mg) of the modified resin prepared according to synthesis method 1 was treated for 1–2 h with CBMIT reagent (5 eq) in dry nitromethane. The resin was collected by filtration and the appropriate aniline (5 eq) in DMA were added and the mixture was kept for 12 h in a suitable vessel on a shaker. The resin was collected by filtration, washed with isopropanol and DCM and treated for 1 h with 50% strength TFA in DCM. The TFA solution was concentrated in vacuo and the crude urea derivative was analysed by analytical HPLC-MS. The crude urea derivative was then purified by preparative HPLC.

Synthesis Method 6

A first aniline derivative (0.1 mmol) was dissolved (or suspended) in dry nitromethane (0.4–1.0 ml) and CBMIT (0.5 ml/0.1 mmol) was added at 0° C. and the mixture was stirred for 1 h. The modified resin (100 mg/0.1 mmol) prepared according to synthesis method 1 were added to this reaction mixture and it was kept for 12 h in a suitable vessel on a shaker. The resin was collected by filtration, washed and treated for 1 h with 50% strength TFA. The TFA solution was collected by filtration and concentrated in vacuo. The crude urea derivative was analysed by analytical HPLC-MS and purified by preparative HPLC.

Synthesis Method 7

To a solution of the of hexafluoroisopropyloxalate in dry DCM or DMF the amine (1.0 eq.) was added. After 24 h at rt the second amine (1.0 eq.) was added. After 2 d at rt the precipitate was filtered. The solvent of the filtrate was removed in vacuo and the product crystallized from methanol or purified by flash chromatography.

Synthesis of N-(4-benzylsulfamoylphenyl)-N'-(3-carbamimidoyl-phenyl)-oxalamide (115)

To a solution of hexafluoroisopropyl oxalate (500 mg, 1.28 mmol) in DCM (5 ml) 3-aminobenzonitrile (1.0 eq. 151 mg) was added. After 24 h at rt the 4-Amino-N-benzylbenzenesulfon-amide (363 mg/1.28 mmol) and N,N-dimethylacetamide (5 ml) were added. After 30 h at rt, 6 h at 40° C. and 20 h at rt the precipitate was filtered. The solvent of the filtrate was removed in vacuo and the nitrile crystallized from MeOH. To the nitrile (50 mg, 115 μmol) a solution of HCl in MeOH (25 ml) and DCM (30 ml) were added at 0° C. After 20 h at rt the solvent was removed and the iminoether dried in vacuo. The iminoether was dissolved in a solution of $NH_3$ in MeOH (4 ml, 7 M) and toluene (3 ml). After 2 h at 60° C. the solvent was removed in vacuo. After dilution in chloroform and MeOH (5 ml each) solid byproducts were removed by filtration. After removal of the solvent purification by flash chromatography (A:AcOEt, B:MEOH, 100→35% A within 25 min) yielded the amidine (50%).

Synthesis of N-(3-benzylsulfamoylphenyl)-N'-(3-carbamimidoyl-phenyl)-oxalamide (116)

The compound was synthesized in the same manner as the 4-benzylsulfamoylphenyl analogue, with the exception that the nitrile was purified by chromatography (with a PE/AcOEt-gradient). The amidine was obtained as a mixture of the free amidine and the acetate.

Synthesis Method 8

The nitrobenzenesulfonylchloride or nitrobenzoylchloride derivate (1 eq.) was added to a solution of benzylamine or its hydrochloride (1–2 eq) and triethylamine or DIEA (1–2 eq.) in dry THF or acetonitrile at 0° C. under inert atmosphere. The reaction mixture was warmed to ambient temperature after 10 min and stirred for a further 18 to 72 h. It was then concentrated in vacuo, water was added and the resulting precipitate was filtered and dried in vacuo. The residue was dissolved in methanol, ethanol or ethanol/ethyl acetate (½) and hydrogenated for 18 h over palladium on charcoal. The mixture was filtered and the filtrate concentrated in vacuo. The residue (1 eq.) was dissolved in anhydrous solvent (DCM, DCM/DMA, THF or THF/DMA) under inert atmosphere, the cyanophenylisocyanate (1 eq.) was added and the mixture was stirred at 20–67° C. for 18 h. The precipitate was filtered and dried in vacuo. If no precipitate formed, the solution was concentrated and the residue crystallized with an appropriate solvent. The urea derivatives thus obtained were recrystallized from ethanol/water if necessary and again dried in vacuo. An aliquot of the substance was dissolved in anhydrous hydrochloric acid solution in methanol at 0° C. and stirred for 18 h, during which the mixture was warmed to ambient temperature. The resulting precipitate was filtered and dried in vacuo. If no precipitate formed, the solution was concentrated and dried in vacuo. In case an unsubstituted amidine was to be synthesized, the residue was dissolved in 7 M methanolic ammonia solution and refluxed for 2 h. If an alkylated amidine or an amidoxime was to be synthesized, the residue was dissolved in methanol or ethanol and triethylamine (0–10 eq.) and the amine or its hydrochloride or hydroxyamine hydrochloride (1–6 eq.) was added and the mixture was refluxed for 18 h. The precipitate was filtered and dried in vacuo. If no precipitate formed, the solution was concentrated in vacuo and purified by column chromatography (silica gel column, ethyl acetate/methanol) or preparative HPLC. For the synthesis of an acylated amidine, the acid chloride (2.5 eq.) was added to the solution of the amidine (1 eq.) and triethylamine (5 eq.) in anhydrous DMA, at 0° C. After 10 min, the mixture was warmed to room temperature and stirred for another 2 h. The precipitate was separated by centrifugation, washed with ethyl acetate/diethylether and dried in vacuo.

Synthesis of 4-[3-(3-carbaminmidoylphenyl)-ureido]-N-(4-sulfamoylbenzyl)-benzamide (84)

A solution of 4-nitrobenzoylchloride (1.85 g, 1 eq.) in acetonitrile (20 ml) was added to a solution of 4-aminomethyl-benzenesulfonamide hydrochloride (4.44 g, 2 eq.) and triethylamine (2.78 ml, 2 eq.) in acetonitrile (40 ml) at 0° C. under inert atmosphere. After the addition was completed, the mixture was warmed to rt and stirred for 3 d. Water was added and the mixture was concentrated under reduced pressure. The resulting precipitate was filtered off and washed with water and methanol to yield 2.86 g (85%) of 4-nitro-N-(4-sulfamoylbenzyl)-benzamide.

4-Nitro-N-(4-sulfamoylbenzyl)-benzamide (2.86 g) was dissolved in methanol (500 ml), palladium on charcoal (1 g, 5%) was added and the mixture hydrogenated overnight. The catalyst was removed by filtration and the filtrate concentrated in vacuo. Yield: 2.13 g (89%) of 4-amino-N-(4-sulfamoylbenzyl)-benzamide.

4-Amino-N-(4-sulfamoylbenzyl)-benzamide (2.13 g, 1 eq.) was dissolved anhydrous in DMA (10 ml) under inert atmosphere, anhydrous DCM (30 ml) was added and the solution was cooled to 0° C. A solution of 3-cyanophenylisocyanate (1.9 g, 1.9 eq.) in anhydrous DCM (10 ml) was added and the mixture stirred over night. The resulting precipitate was filtered off, washed with methanol and dried in vacuo to yield 2.38 g (76%) 4-[3-(3-cyanophenyl)-ureido]-N-(4-sulfamoylbenzyl)-benzamide.

4-[3-(3-Cyanophenyl)ureido]-N-(4-sulfamoylbenzyl)-benzamide (449 mg) was suspended in methanolic hydrochloride acid solution (50 ml) at 0° C. under inert atmosphere and stirred for 20 h during which the mixture was warmed to rt. The precipitate was filtered off, washed with methanol and dried in vacuo. Yield: 0.37 g (77%) of 3-{3-[4-(4-sulfamoylbenzylcarbamoyl)phenyl]ureido}-benzimidic acid methyl ester.

3-{3-[4-(4-Sulfamoylbenzylcarbamoyl)-phenyl]-ureido}-benzimidic acid methyl ester (370 mg) was dissolved in methanolic ammonia solution (5 ml, 7 M) and refluxed for 4 h. The mixture was filtered, the filtrate concentrated in vacuo and diethylether was added. The resulting precipitate (300 mg) was filtered off. 100 mg were suspended in ethyl acetate/methanol/ammonia, filtered off, washed with ethyl acetate and ether and dried in vacuo to yield 60 mg of 4-[3-(3-carbamimidoylphenyl)-ureido]-N-(4-sulfamoylbenzyl)-benzamide.

Synthesis of 3-{3-[4-(4-nitrobenzenesulfonyl)-phenyl]-ureido}-benzamidine (74)

A solution of 3-cyanophenylisocyanate (1 g, 1 eq.) in anhydrous DCM (10 ml) was added to a solution of 4-(4-nitro-phenylsulfonyl)aniline (2 g, 1 eq.) in anhydrous DCM (40 ml) under inert atmosphere. The mixture was stirred at rt for 1 d, then refluxed for 1 d. The precipitate was filtered off, refluxed in ethanol for 2 h, filtered off again and dried in vacuo. Yield: 1.65 g (54%) of 1-(3-cyanophenyl)-3-[4-(4-nitrobenzenesulfonyl)-phenyl]-urea.

1-(3-Cyanophenyl)-3-[4-(4-nitrobenzenesulfonyl)-phenyl]-urea (500 mg) was suspended in methanolic hydrochloride acid solution (150 ml) at 0° C. under inert atmosphere and stirred for 2 d during which the mixture was warmed to rt. The precipitate was filtered off and dried in vacuo to give 3-{3-[4-(4-nitrobenzenesulfonyl)-phenyl]-ureido}-benzimidic acid methyl ester. This was suspended in methanolic ammonia solution (4 ml, 7 M), the mixture was refluxed for 2 h and cooled to rt. The precipitate was filtered off and dried in vacuo to yield 132 mg (26% over 2 steps) of 3-{3-[4-(4-nitrobenzene-sulfonyl)-phenyl]-ureido}-benzamidine.

Synthesis of 4-{3-[4-(4-nitrobenzenesulfonyl)-phenyl]-ureido}-N-pyridine-3-yl-benzamidine (95)

3-{3-[4-(4-Nitrobenzenesulfonyl)-phenyl]-ureido}-benzimidic acid methyl ester (50 mg, 1 eq) was suspended in methanol (10 ml) and 3-aminopyridine (12 mg, 1.2 eq) was added. The solution was stirred for 72 h at 70° C. The precipitate was filtered off and dried in vacuo.

Synthesis of 3-[3-(4-benzylsulfamoylphenyl)-ureido]-benzamidine (38)

A solution of p-Nitrobenzenesulfonylchloride (274 g, 1.2 eq) in DCM (1 l), was added to a solution of benzylamine (500 g, 1 eq) and triethylamine (469 ml, 1.5 eq) in DCM (1 l) at 4° C. in small portions and then stirred for 1 h. Afterwards the mixture was stirred at rt for 16 h. The solvent was removed in vacuo and the residue was washed with a mixture of DCM/PE (1/1) at 4° C., filtered and dried in vacuo to give N-Benzyl-4-nitrobenzenesulfonamide. Yield 90%.

N-benzyl-4-nitrobenzenesulfonamid (60 g, 1 eq) was dissolved in anhydrous ethanol (2 l) and Pd/C (10 g, 1 eq) was added under inert atmosphere. The mixture was stirred under a hydrogen atmosphere for 8 h. Then the solution was filtered over Celite, concentrated in vacuo to ~40 ml and then crystallized. The product was washed twice with ethanol (20 ml) at 4° C., filtered and dried in vacuo to give 4-amino-N-benzylbenzenesulfonamide. Yield 75%.

A solution of 3-cyanophenylisocyanate (6.4 g, 1 eq) in DCM (100 ml), was added to 4-amino-N-benzylbenzenesulfonamide (10.4 g, 1 eq), dissolved in DCM (100 ml), at 4° C. in small portions, stirred for 1 h. Afterwards the mixture was stirred at rt for 16 h. The solvent was removed in vacuo and the residue was recrystallized from ethanol/water (1/1). The product was filtered, washed 2 times with ethanol/water (1/1) at 4° C., and dried in vacuo to give N-benzyl-4-[3-(3-cyanophenyl)-ureido]-benzenesulfonamide. Yield 90% N-benzyl-4-[3-(3-cyanophenyl)-ureido]-benzenesulfonamide (22 g, 1 eq) was dissolved in ethanol (150 ml). Hydrochloric acid was bubbled through the solution for 2 h at 4° C. Then the solution was stirred for 1 h at rt. The solvent was removed in vacuo. The product was washed with ethanol/water (1/1) at 4° C., and dried in vacuo to give 3-[3-(4-benzylsulfamoylphenyl)-ureido]-benzimidic acid ethyl ester. Yield 75%.

3-[3-(4-benzylsulfamoylphenyl)-ureido]-benzimidic acid ethyl ester (21 g, 1 eq) was dissolved in ethanol (150 ml). $NH_3$ was bubbled through the solution for 3 h. Then the solution was stirred for 2 h at rt. The solvent was removed in vacuo and the residue recrystallized from ethanol/water (1/1). The pure product was dissolved at 80° C. in ethanol (200 ml) and etheric hydrochloridic acid (200 ml, 1 M) was added. The mixture was filled up to a volume of 1 l with ether, the resulting precipitate was filtered and dried in vacuo to give over 3-[3-(4-Benzylsulfamoyl-phenyl)-ureido]-benzamidine Yield 84%.

Synthesis Method 9

Aminobenzonitrile (1 eq.) and chlorosulfonylphenylisocyanate (1 eq) were dissolved in anhydrous dichloromethane under inert atmosphere and stirred at ambient temperature for 18 h. The precipitate was filtered off and dried in vacuo or else the reaction mixture was concentrated to dryness in vacuo. The dry substance (1 eq) was added to a solution of the benzylamine (1–2 eq.) and triethylamine (1–2 eq.) in anhydrous acetonitrile at 0° C. under inert atmosphere. The reaction mixture was warmed to ambient temperature for 10 min and stirred for a further 18 h. It was then concentrated in vacuo, water was added and the resulting precipitate was filtered and dried in vacuo. Further reactions and purifications according to synthesis method 8.

Synthesis of 3-{3-[4-(4-sulfamoyl-benzylsulfamoyl)-phenyl]-ureido}-benzamidine (40)

A solution of 5.00 g (1 eq.) of 4-chlorosulfonylphenylisocyanate in anhydrous DCM (40 ml) was added to a solution of 3-aminobenzonitrile (2.71 g, 1 eq.) in anhydrous isocyanate (60 ml) at rt under inert atmosphere and the mixture was stirred overnight. The precipitate was filtered off to yield 7.3 g (95%) of 4-[3-(3-cyanophenyl)-ureido]-benzenesulfonyl chloride.

4-[3-(3-Cyanophenyl)-ureido]-benzenesulfonylchloride (5.04 g, 1 eq.) was added in portions to a solution of 4-aminomethyl-benzenesulfonamide hydrochloride (6.68 g, 2 eq.) and triethylamine (8.32 ml, 2 eq.) in acetonitrile (100 ml) at 0° C. under inert atmosphere. The mixture was warmed to rt, stirred for 3 d and then concentrated in vacuo. Water was added and the resulting precipitate filtered off and dried in vacuo. Yield: 7.27 g (99.7%) of [3-(3-cyanophenyl)-ureido]-N-(4-sulfonamidobenzyl)-4-benzenesulfonamide.

[3-(3-cyanophenyl)-ureido]-N-(4-sulfonamidobenzyl)-4-benzene-sulfonamide (1 g) was suspended in methanolic hydrochloridic acid (100 ml) at 0° C. under inert atmosphere and stirred for 20 h during which the mixture warmed to rt. The solution was concentrated under reduced pressure and diethylether was added. The resulting precipitate was filtered off, washed with diethylether and dried in vacuo. Yield: 849 mg (78%) of 3-{3-[4-(4-sulfamoylbenzylsulfamoyl)-phenyl]-ureido}-benzimidic acid methyl ester.

3-{3-[4-(4-Sulfamoyl-benzylsulfamoyl)-phenyl]-ureido}-benz-amidine (849 mg) were dissolved in methanolic ammonia solution (5 ml, 7 M) and refluxed for 2 h. The precipitate was filtered off and dried in vacuo to yield 719 mg (87%) of 3-{3-[4-(4-sulfamoylbenzylsulfamoyl)-phenyl]-ureido}-benzamidine. Anayltical data see table 1.

Synthesis of 3-{3-[4-(3-trifluoromethyl-benzylsulfamoyl)-phenyl]-ureido}-benzamidine (42)

3-Trifluoromethylbenzylamine (0.52 g, 1 eq.) was added to a solution of 4-[3-(3-cyanophenyl)-ureido]-benzenesulfonyl chloride (1 g, 1 eq.) and triethylamine (1.05 ml, 1.6 eq.) in acetonitrile (10 ml) under inert atmosphere. The mixture was stirred for 3 d, concentrated in vacuo and water was added. The resulting precipitate was filtered off and dried in vacuo to yield 1.37 g (97%) of 4-[3-(3-cyanophenyl)-ureido]-N-(3-trifluoromethylbenzyl)-benzenesulfonamide.

4-[3-(3-Cyanophenyl)-ureido]-N-(3-trifluoromethylbenzyl)-benzenesulfonamide (500 mg) were suspended in methanolic hydrochloridic acid (75 ml) at 0° C. under inert atmosphere and stirred for 2 d during which the mixture warmed to rt. The solution was concentrated to dryness in vacuo. The residue was dissolved in methanolic ammonia solution (6 ml, 7 M), the solution was refluxed for 2 h, concentrated in vacuo and purified by column chromatography (silica gel, ethyl acetate/methanol 7/1). Yield: 319 mg of 3-{3-[4-(3-trifluoro-methylbenzylsulfamoyl)-phenyl]-ureido}-benzamidine.

Synthesis of 4-{3-[4-(4-sulfamoylbenzylsulfamoyl)-phenyl]-ureido}-benzamidine (62)

4-Cyanophenylisocyanate (190 mg, 1.5 eq.) was added in portions to a solution of 4-amino-N-(4-sulfamoylbenzyl)-benzamide (300 mg) in anhydrous THF (20 ml) under inert atmosphere and the mixture was refluxed for 7 h. The resulting precipitate was filtered off and dried in vacuo. The dry substance (200 mg) was suspended in methanolic hydrochloridic acid (75 ml) at 0° C. under inert atmosphere and stirred overnight during which the mixture was warmed to rt. The solution was concentrated in vacuo and the resulting precipitate filtered off after 5 h of storage at 4° C. After drying in vacuo overnight, the precipitate was suspended in methanolic ammonia solution (5 ml, 7 M) and the mixture was refluxed for 4 h, cooled to rt and the resulting precipitate filtered off in vacuo. Yield: 110 mg (53% over 2 steps) of 4-{3-[4-(4-sulfamoylbenzylsulfamoyl)-phenyl]-ureido}-benzamidine.

Synthesis of 4-{3-[3-(4,5-dihydro-1H-imidazol-2-yl)-phenyl]-ureido}-N-(4-sulfamoylbenzyl)-benzenesulfonamide (112)

3-{3-[4-(4-Sulfamoylbenzylsulfamoyl)-phenyl]-ureido}-benzimidic acid methyl ester (130 mg, 1 eq.) was suspended in anhydrous ethanol (10 ml), ethylenediamine (0.1 ml, 5.7 eq.) was added and the mixture was refluxed for 16 h. The precipitate was filtered off, washed with diethylether and dried in vacuo. Yield: 60 mg (45%) of 4-{3-[4-(4,5-dihydro-1H-imidazol-2-yl)-phenyl]-ureido}-N-(4-sulfamoylbenzyl)-benzenesulfonamide.

Synthesis of 3-{3-[4-(2,3,6-trifluorobenzylsulfamoyl)-phenyl]-ureido}-benzamidine (91)

4-[3-(3-Cyanophenyl)-ureido]-benzenesulfonyl chloride (1.0 g, 2.98 mmol) was dissolved in 20 ml THF, 2,3,6-trifluoro-benzylamine (0.48 g, 2.98 mmol) and DIEA (0.52 ml, 2.98 mmol) were added and the solution was refluxed for about 3 h. The solvent was removed in vacuo and the residue cristallized with ethanol/water. The solid was filtered and dried in vacuo. Yield 94% of 4-[3-(3-cyano-phenyl)-ureido]-N-(2,3,6-trifluorobenzyl)-benzenesulfonamide.

4-[3-(3-Cyanophenyl)-ureido]-N-(2,3,6-trifluorobenzyl)-benzenesulfonamide (230 mg, 0.5 mmol) was dissolved in HCl/MeOH (25 ml, 7 M) at 0° C. under inert atmosphere and stirred overnight at rt. The solution was concentrated and dried in vacuo to yield 99% of 3-{3-[4-(2,3,6-trifluorobenzyl-sulfamoyl)-phenyl]-ureido}-benzimidic acid methyl ester.

3-{3-[4-(2,3,6-Trifluorobenzylsulfamoyl)-phenyl]-ureido}-benzimidic acid methyl ester (250 mg, 0.5 mmol) was dissolved in NH$_3$/MeOH (15 ml, 7 M). The solution was stirred overnight at rt. Further 10 ml of NH$_3$/MeOH (7 M) were added and the mixture stirred for 3 h at 65° C. The solvents were evaporated and the solid residue purified by flash chromatography on silica gel with a gradient of AcOEt and MeOH. The fractions with the desired product were collected, evaporated and the product crystallized from MeOH/Et$_2$O. Yield 50%.

Synthesis of 3-{3-[4-(benzhydrylsulfamoyl)-phenyl]-ureido}-benzamidine (24)

N-Benzhydryl-4-[3-(3-cyanophenyl)-ureido]-benzenesulfonamide (500 mg, 1.04 mmol, synthesized according to general method 8) was diluted in a mixture of MeOH (35 ml) and toluene (10 ml). NH$_2$OH—HCl (220 mg, 3.11 mmol) and DIPEA (0.9 ml) were added and the reaction was stirred at 60° C. After complete turnover of the nitrile to the amidoxime (e.g. 1–2 d) the solvent was removed in vacuo. Inorganic salts were separated by filtration over silica. Thus the amidoxime and as byproduct the amide were obtained. To a solution of the amidoxime in acetic acid (40 ml) and MeOH (80 ml), Ac$_2$O (263 µl, 2.5 mmol) was added at 0° C. As soon as the turnover of the amidoxime to the acetate (e.g. 30 min) was complete, zinc powder (327 mg, 5 eq) was added. After reduction to the amidine the solvent was removed in vacuo, and the precipitate was portioned between water and ethylacetate. The product was extracted with ethylacetate, the solvent of the combined organic layers was removed in vacuo and the amidine purified by chromatography (AcOEt/MeOH-gradient) to yield the amidine (14%).

Biological Activity

1. Antiplasmodial Activity

For the determination of the antiplasmodial activity of the compounds, the multiresistant Dd2 strain of *Plasmodium falciparum* was used. The incorporation of [8-$^3$H]

hypoxanthine into the parasitic nucleic acids was measured. The plasmodia were incubated at 0.3% parasitaemia and an erythrocyte haematocrit of 2.5% in the presence of different concentrations of the compounds in a final volume of 200 µl. The medium employed was RPMI 1640 which contained 10% of heat-treated human serum and 3 mg/l of gentamycin. In the incubations, the concentrations of the compounds varied from 0.3 to 100 µM. After 48 h, each batch was treated with 50 µl of [8-$^3$H]hypoxanthine (1 mCi/ml) and incubated for a further 18 h. The cells were filtered off, washed and suspended in 20 µl of scintillation fluid. The radioactive hypoxanthine absorbed by the parasites was then quantified using a scintillation counter.

The results were presented graphically and the $IC_{50}$ value was determined using a fitting function. The value $IC_{50}$, the 'inhibition constant', indicates the value in µMol/l at which 50% inhibition occurs.

Antiplasmodial activity against the 3D7 chloroquine sensitive strain of *Plasmodium falciparum* was determined as described elsewhere (J. Med. Chem. (2001) 44(19), 3187–3194).

2. Inhibition of Human 20S Proteasome

The activity of human 20S proteasome is measured by monitoring the release of AMC (7-Amino-4-methylcoumarin) from the fluorogenic peptide Suc-Leu-Leu-Val-Tyr-AMC (provided by Bachem, Germany).

The test compound is incubated with 0,25 µg human 20S proteasome (Biotrend, Germany) in the assay buffer (25 mM Hepes, 500 µM EDTA, 3% SDS, pH 7.6) for 10 min in a final volume of 200 µl. The reaction is started by adding the fluorogenic peptide substrate. The mixture is incubated for 30 min at 37° C. Meanwhile the rate of AMC release is measured by monitoring the increase of fluorescence every 30 seconds (excitation 390 nm, emission 460 nm). The test item is added at a concentration of 5 or 50 µM for initial determination of inhibition. For the determination of $IC_{50}$-values, the inhibitor is added in a suited dilution series in general with a final concentration between 5 and 0,005 µM.

The value $IC_{50}$, the 'inhibition constant', indicates the value in µMol/l at which 50% inhibition occurs.

Table 1 shows Examples of structures, analytical data, in vitro antiplasmodial activity and human proteasome inhibition of tested compounds (antiplasmodial activity is defined A: $IC_{50}$ value <1 µM; B: $IC_{50}$ value 1–10 µM; C: $IC_{50}$ value 10–100 µM. Human proteasome inhibition is defined: A: 90–100% inhibition, B: 75–90% inhibition, C: 50–75% inhibition at a fixed inhibitor concentration of 5 or 50 AM as depicted. An Asterix indicates inhibitors of the human proteasome with an $IC_{50}$ value <1 µM). For abbreviations used as well as experimental details see section "Examples" and "Biological activity".

Table 2 shows NMR Data of selected compounds. For abbreviations see section "Examples".

TABLE 1

| N. | structure | synthesis method | MS | antiplasmodial activity (Dd2) | antiplasmodial activity (3D7) | human proteasome inhibition |
|---|---|---|---|---|---|---|
| 1 | 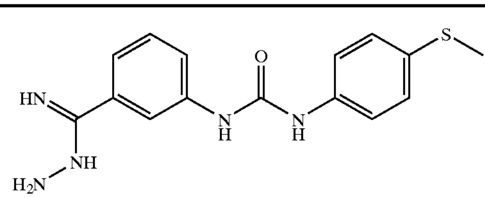 | 2 | 316[M + H] | B | | |
| 2 | 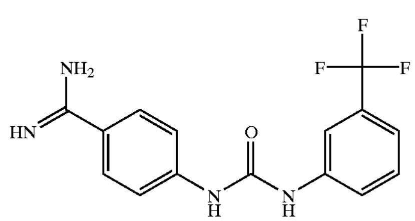 | 2 | 323[M + H] | B | | C(5 µM) |
| 3 | 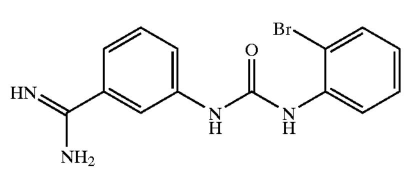 | 2 | 334[M + H] | B | | |
| 4 | 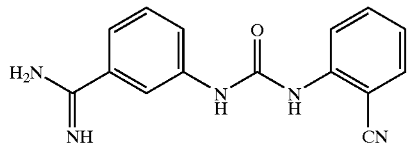 | 4 | 280[M + H] | B | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 5 | 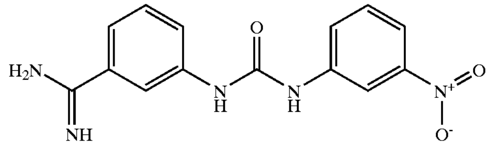 | 4 | 300[M + H] | C | B | |
| 6 | 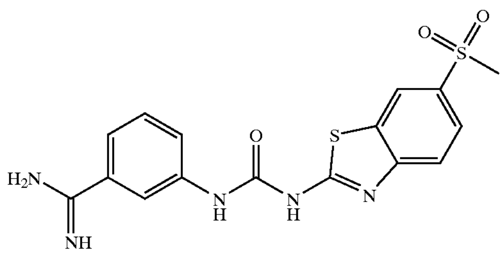 | 4 | 390[M + H] | C | | |
| 7 | 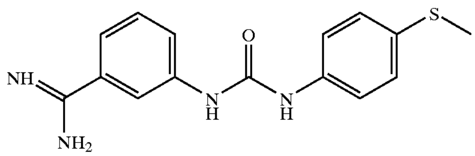 | 2 | 301[M + H] | B | | |
| 8 | 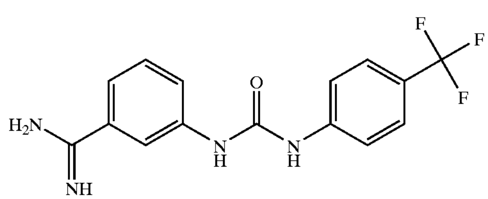 | 4 | 323[M + H] | B | | |
| 9 | 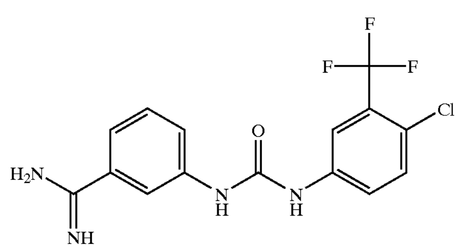 | 4 | 358[M + H] | A | | |
| 10 | 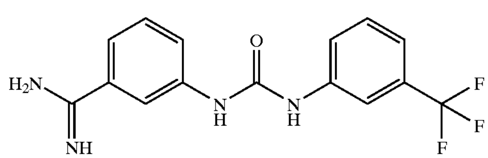 | 4 | 323[M + H] | B | B | |
| 11 | 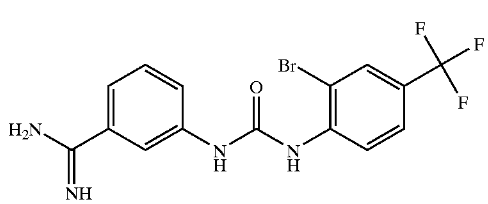 | 4 | 402[M + H] | B | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 12 | 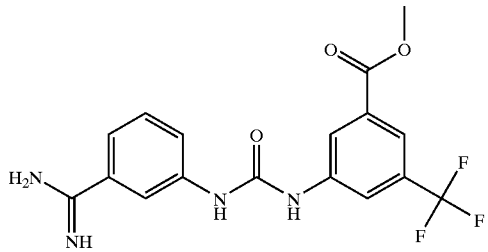 | 4 | 381[M + H] | B | | |
| 13 | 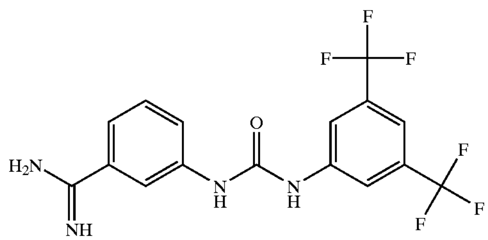 | 4 | 391[M + H] | B | B | |
| 14 | 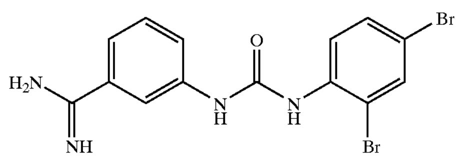 | 4 | 413[M + H] | B | | |
| 15 | 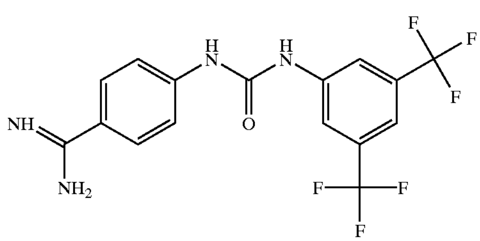 | 4 | 391[M + H]<br>389[M − H] | B | B | |
| 16 | 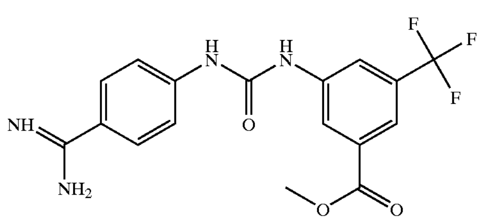 | 4 | 381[M + H]<br>379[M − H] | B | | |
| 17 | 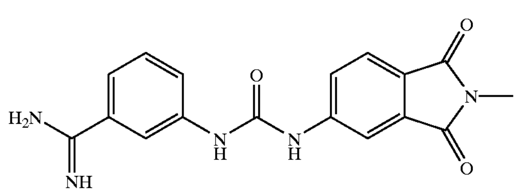 | 4 | 338[M + H] | C | | |
| 18 | 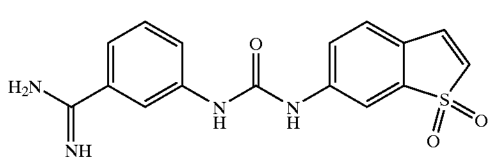 | 4 | 343[M + H] | A | A | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 19 | 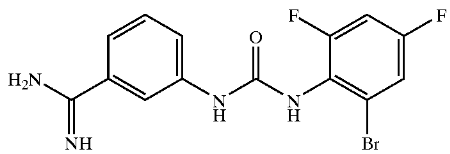 | 4 | 370[M + H] | B | | |
| 20 | 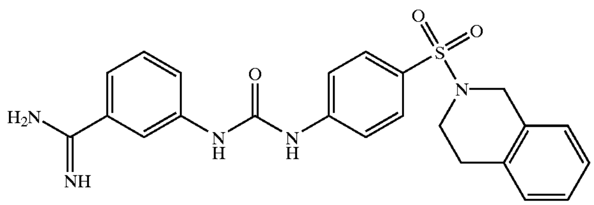 | 3 | 450[M + H] | B | | |
| 21 | 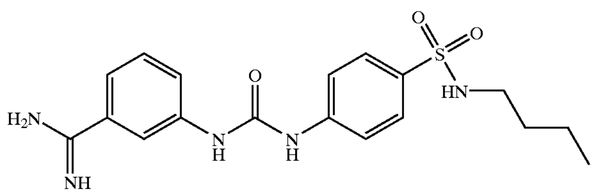 | 3 | 390[M + H] | B | | |
| 22 | 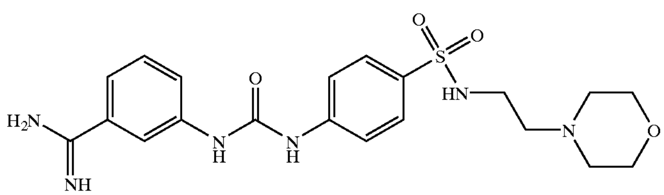 | 9 | 447[M + H] | | | B(5 μM) |
| 23 | 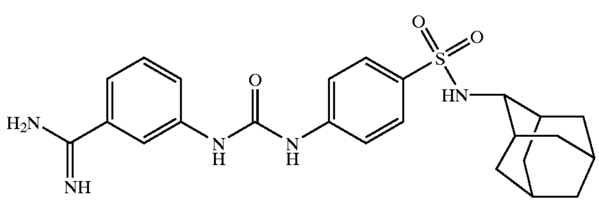 | 3 | 468[M + H] | C | | |
| 24 | 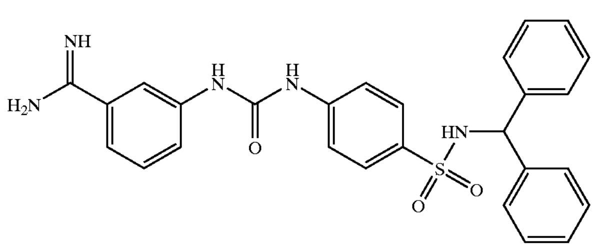 | 3 | 500[M + H] | A | | |
| 25 | 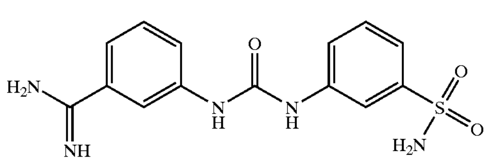 | 4 | 334[M + H] | C | C | A(50 μM)* |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 26 | 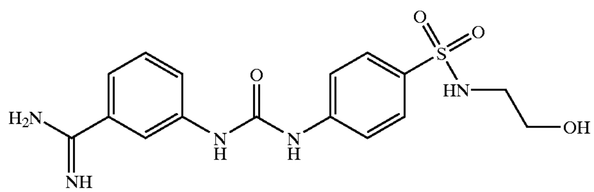 | 4 | 378[M + H] | A | B | |
| 27 | 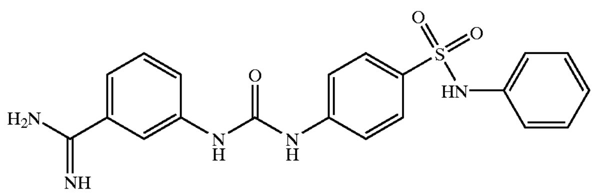 | 3 | 410[M + H] | B | | A(50 μM) |
| 28 | 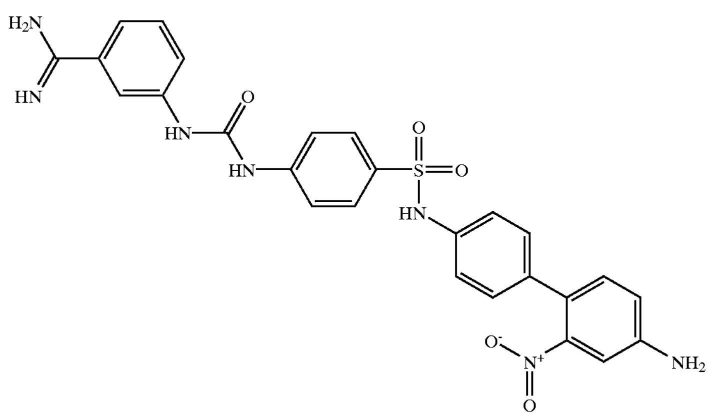 | 3 | 546[M + H] | B | | |
| 29 | 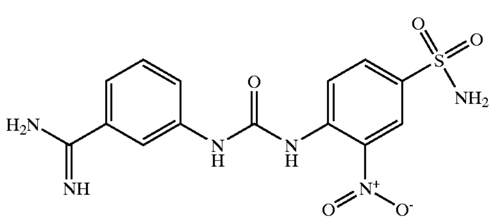 | 4 | 379[M + H] | B | | |
| 30 | 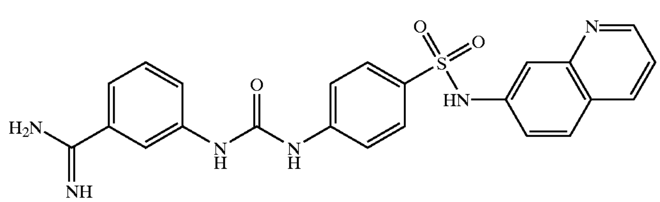 | 3 | 461[M + H] | B | | |
| 31 | 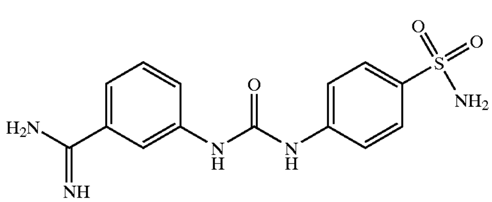 | 4 | 334[M + H] | B | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 32 | 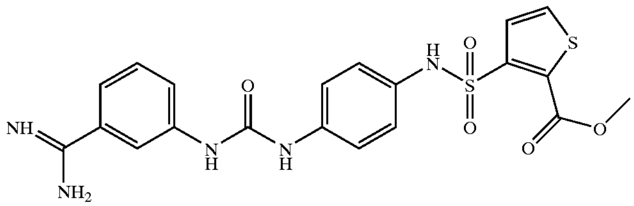 | 2a | 474[M + H] | | | A(5 μM)* |
| 33 | 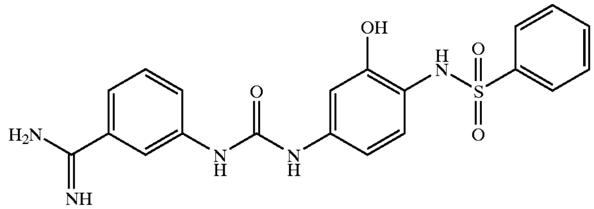 | 4 | 424[M − H] | B | | |
| 34 | 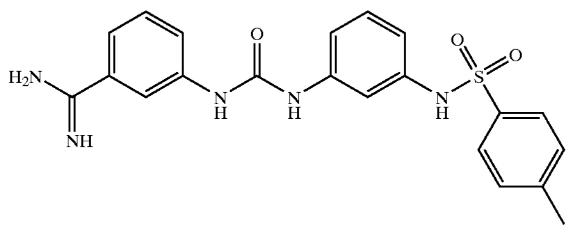 | 2a | 424[M + H] | C | | A(50 μM) |
| 35 | 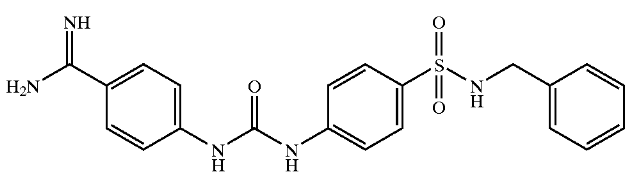 | 9 | 424[M + H]<br>422[M − H] | A | | A(5 μM)* |
| 36 | 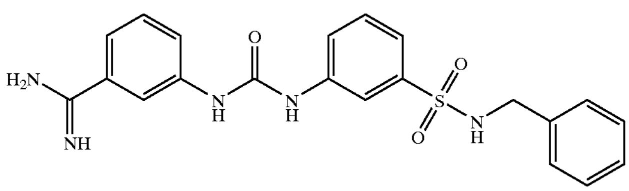 | 8 | 424[M + H]<br>422[M − H] | B | | |
| 37 | 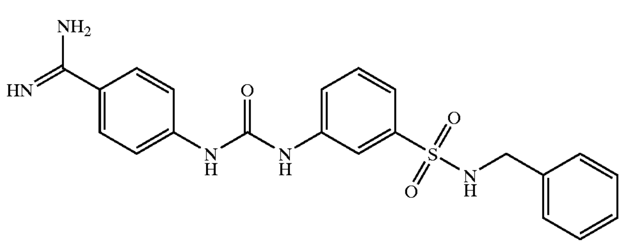 | 8 | 424[M + H]<br>422[M − H] | A | | |
| 38 | 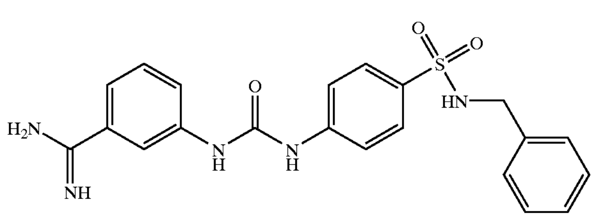 | 8 | 424[M + H] | A | B | A(50 μM)* |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 39 | 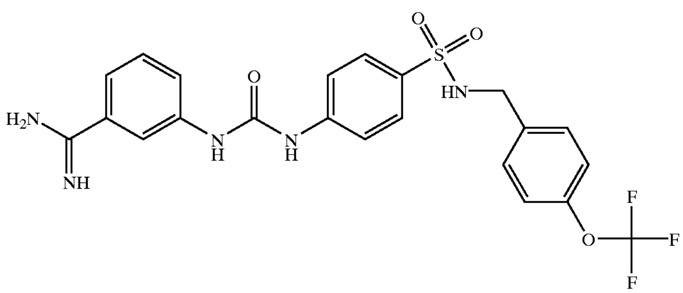 | 9 | 508[M + H]<br>506[M − H] | A | B | |
| 40 | 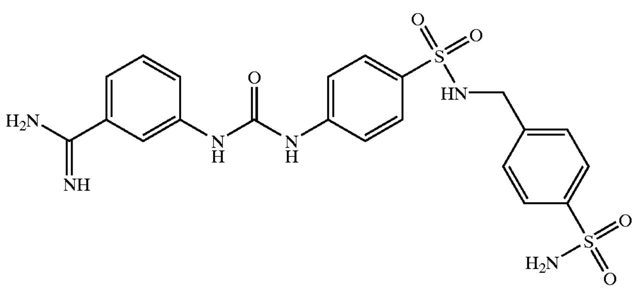 | 9 | 503[M + H]<br>501[M − H] | A | A | A(50 μM)* |
| 41 | 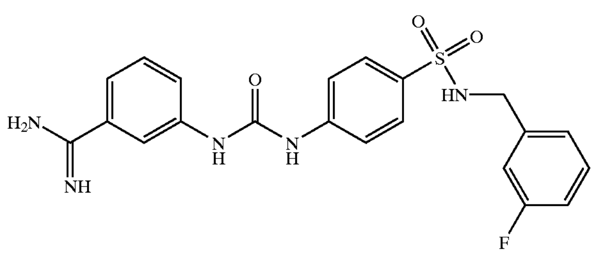 | 8 | 442[M + H]<br>440[M − H] | A | | A(5 μM)* |
| 42 | 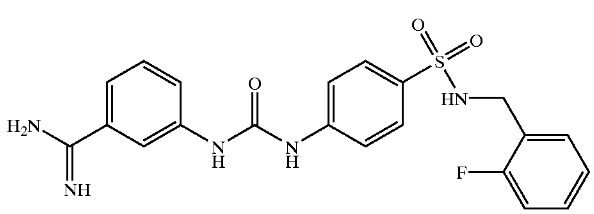 | 9 | 442[M + H]<br>440[M − H] | A | | A(5 μM) |
| 43 | 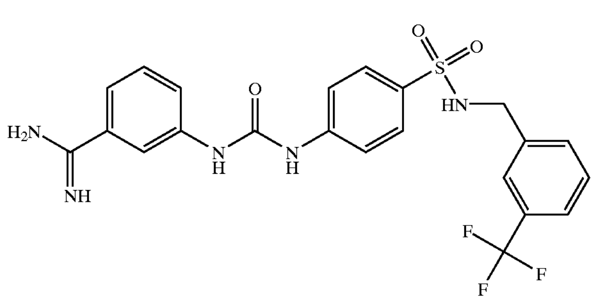 | 9 | 492[M + H]<br>490[M − H] | A | | A(5 μM)* |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 44 | 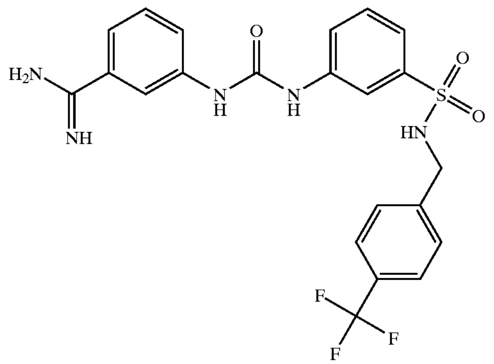 | 8 | 492[M + H] | | | A(50 μM)* |
| 45 | 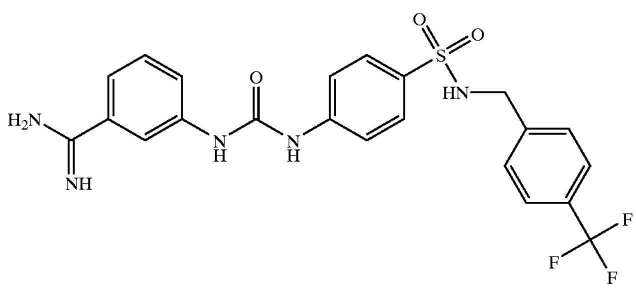 | 8 | 492[M + H]<br>490[M − H] | A | A | A(5 μM)* |
| 46 | 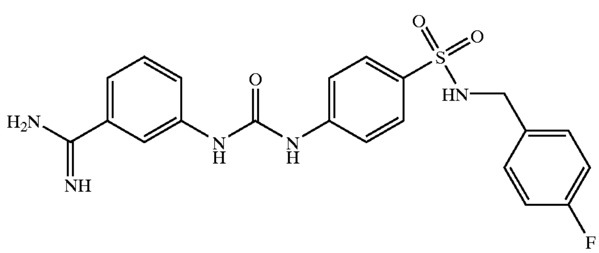 | 8 | 442[M + H]<br>440[M − H] | A | | A(50 μM)* |
| 47 | 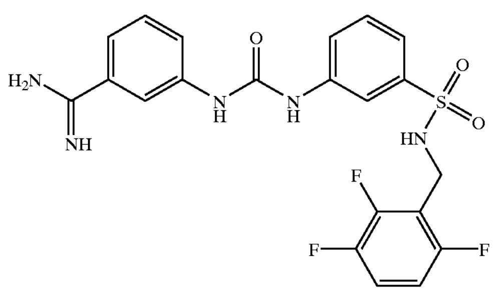 | | 478[M + H] | | | A(50 μM) |
| 48 | 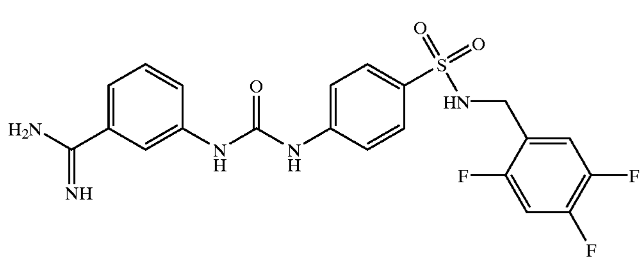 | 9 | 478[M + H] | B | | A(50 μM)* |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 49 | 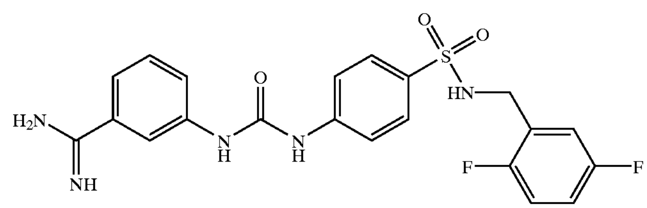 | 9 | 460[M + H]<br>458[M − H] | A | | A(5 μM)* |
| 50 | 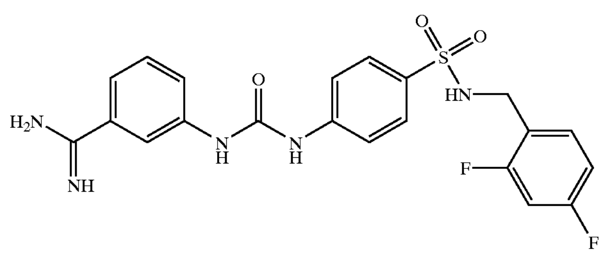 | 9 | 460[M + H]<br>458[M − H] | B | | A(5 μM)* |
| 51 | 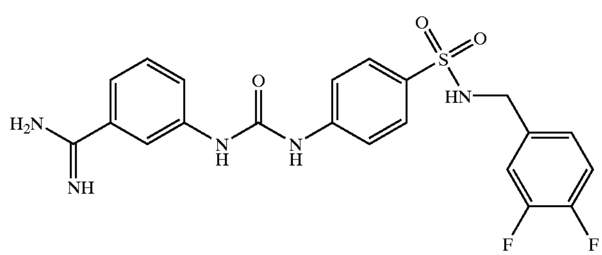 | 9 | 460[M + H)<br>458[M − H] | B | | A(5 μM)* |
| 52 | 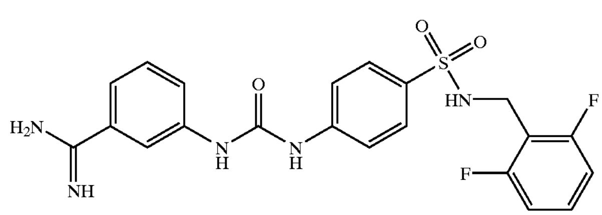 | 9 | 460[M + H]<br>458[M − H] | A | | A(5 μM) |
| 53 | 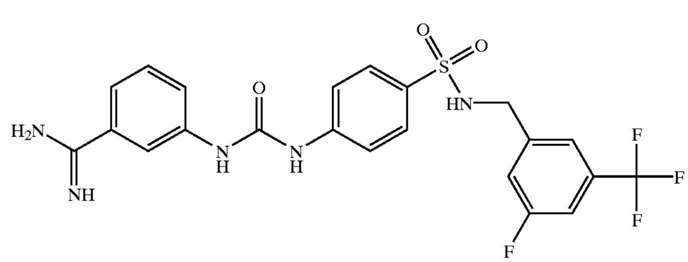 | 8 | 510[M + H] | B | | |
| 54 | 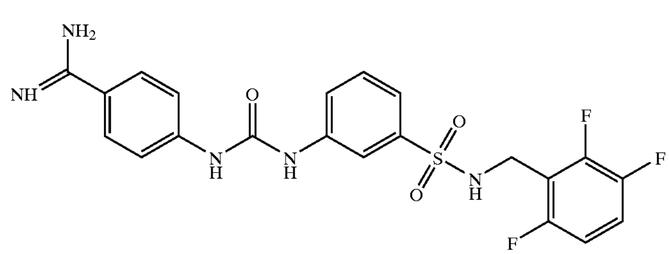 | 8 | 478[M + H] | | | A(50 μM)* |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 55 | 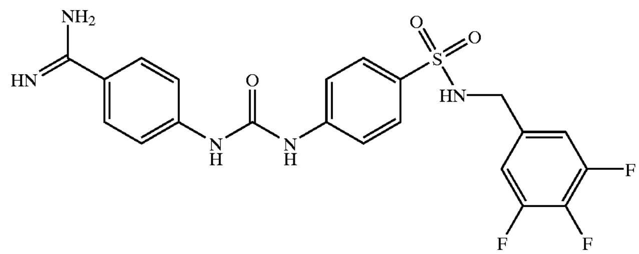 | 9 | 478[M + H]<br>476[M − H] | | | A(5 μM)* |
| 56 | 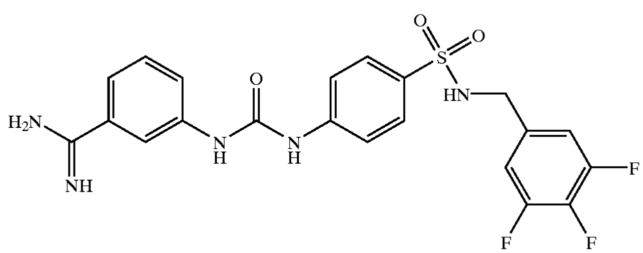 | 9 | 478[M + H]<br>476[M − H] | | | A(5 μM)* |
| 57 | 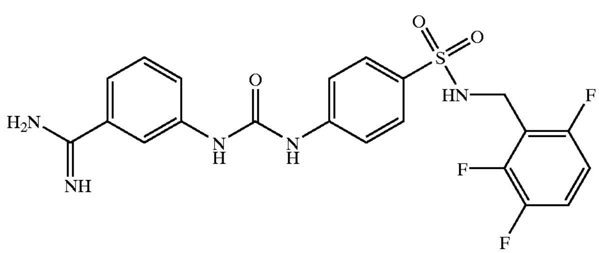 | 9 | 478[M + H] | A | | A(50 μM)* |
| 58 | 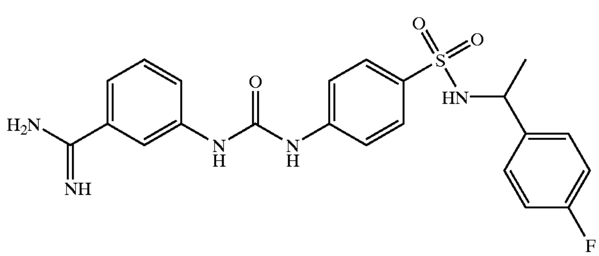 | 3 | 456[M + H]<br>454[M − H] | B | | |
| 59 | 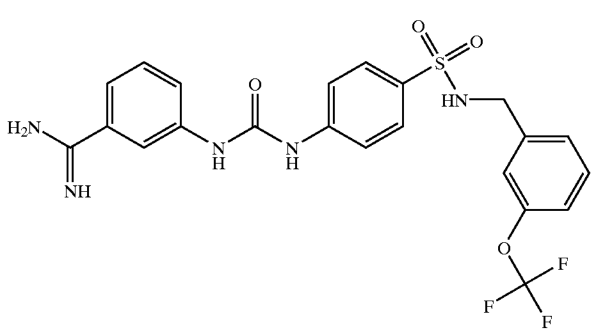 | 8 | 508[M + H] | B | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 60 | 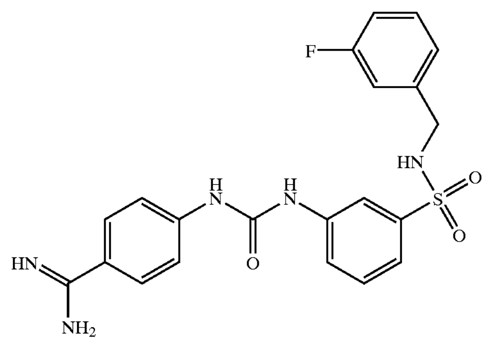 | 8 | 442[M + H]<br>440[M − H] | A | | |
| 61 | 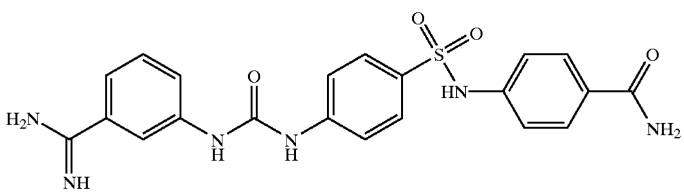 | 9 | 453[M + H]<br>451[M − H] | | | A(5 μM)* |
| 62 | 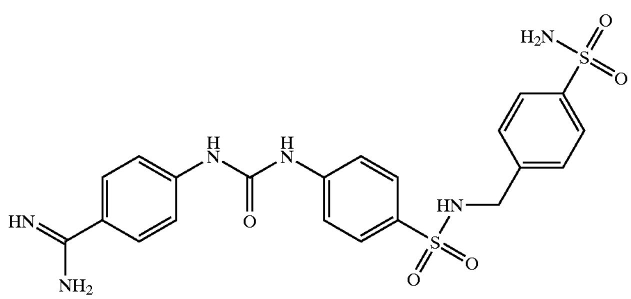 | 9 | 503[M + H]<br>501[M − H] | A | A | A(50 μM)* |
| 63 | 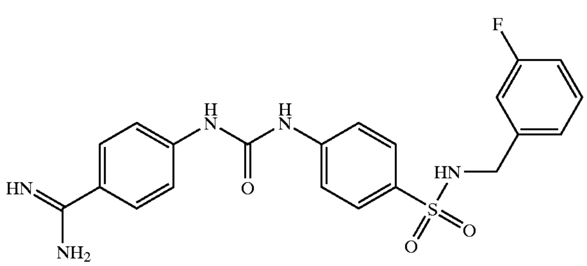 | 9 | 442[M + H]<br>440[M − H] | A | A | |
| 64 | 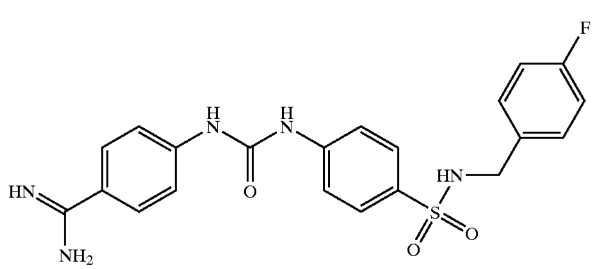 | 8 | 442[M + H]<br>440[M − H] | A | | B(5 μM)* |

TABLE 1-continued
| N. | structure | synthesis method | MS | anti-plasmodial activity (Dd2) | anti-plasmodial activity (3D7) | human proteasome inhibition |
|---|---|---|---|---|---|---|
| 65 | 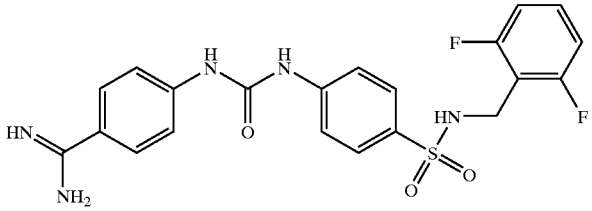 | 9 | 460[M + H]<br>458[M − H] | A | | A(5 μM)* |
| 66 | 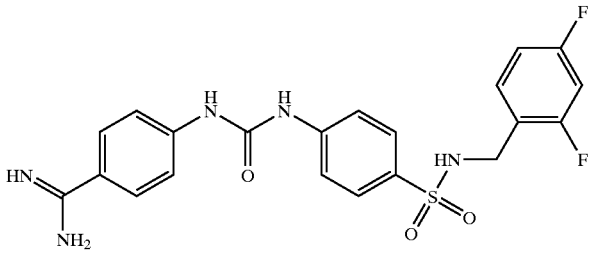 | 9 | 460[M + H]<br>458[M − H] | A | | A(5 μM)* |
| 67 | 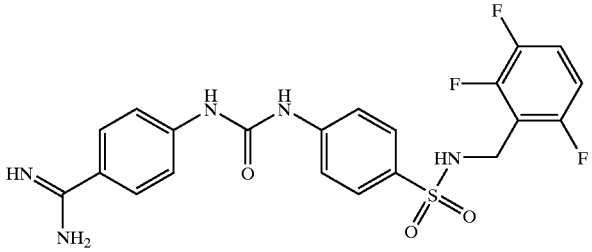 | 9 | 478[M + H] | A | A | |
| 68 | 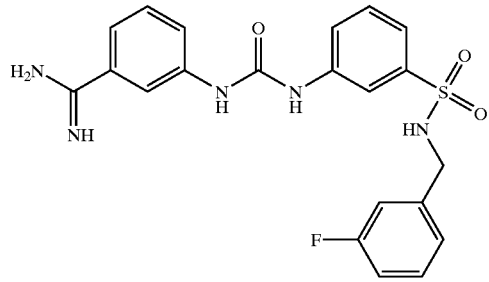 | 8 | 442[M + H]<br>440[M − H] | B | | A(5 μM) |
| 69 | 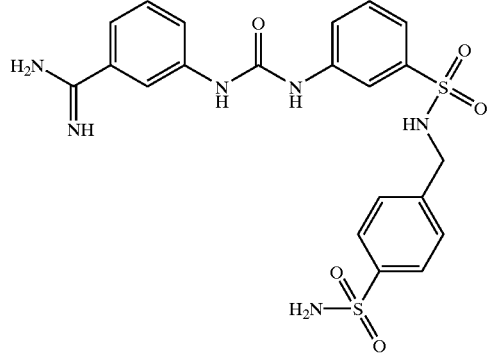 | 8 | 503[M + H]<br>501[M − H] | B | | A(5 μM) |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 70 | 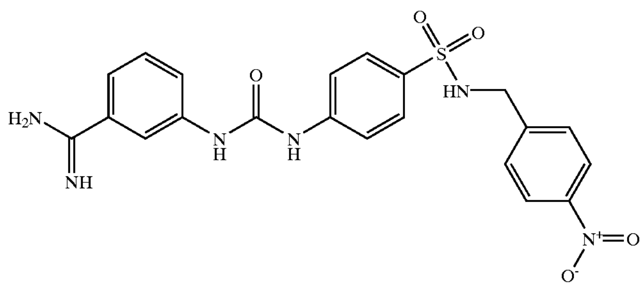 | 9 | 469[M + H]<br>467[M − H] | A | | A(5 μM)* |
| 71 | 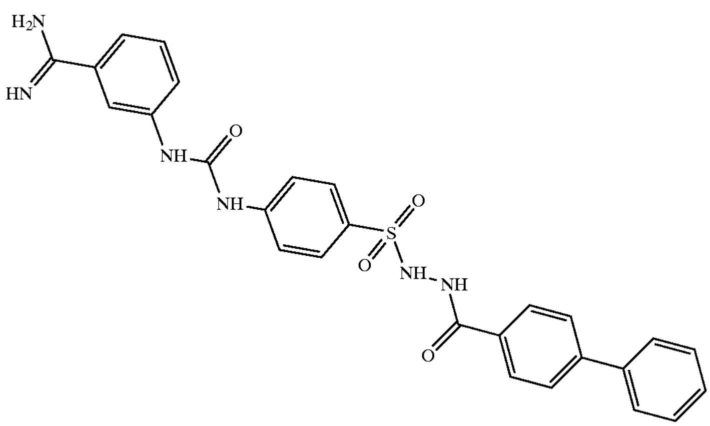 | 3 | 529[M + H] | B | | A(50 μM) |
| 72 | 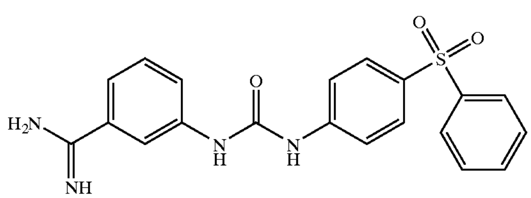 | 4 | 395[M + H] | B | B | |
| 73 | 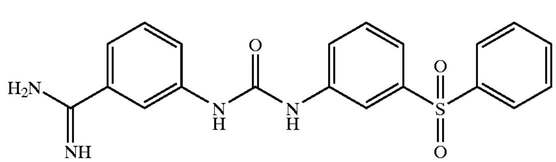 | 4 | 395[M + H] | B | B | |
| 74 | 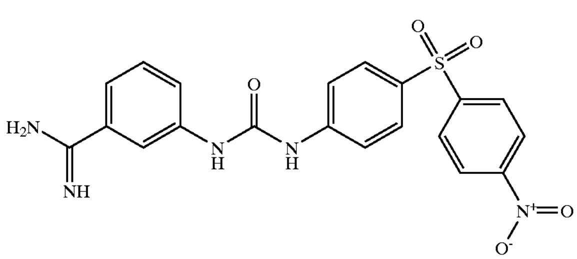 | 8 | 440[M + H] | A | | B(5 μM)* |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 75 | 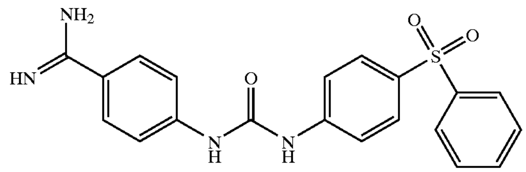 | 4 | 395[M + H]<br>393[M − H] | A | B | |
| 76 | 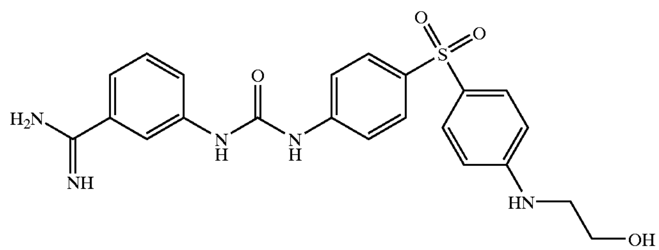 | 4 | 454[M + H] | B | | |
| 77 | 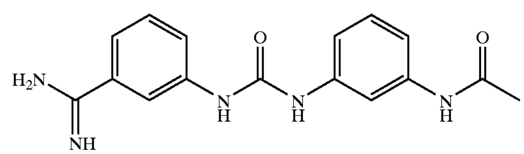 | 4 | 312[M + H] | B | | |
| 78 | 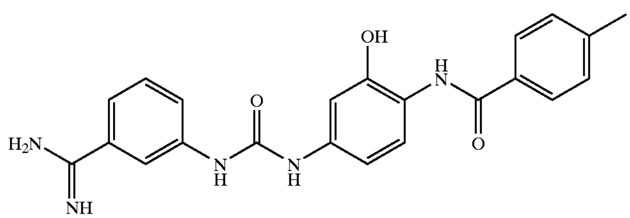 | 4 | 404[M + H] | B | B | |
| 79 | 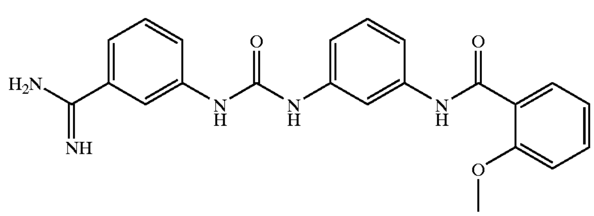 | 2 | 404[M + H] | B | | |
| 80 | 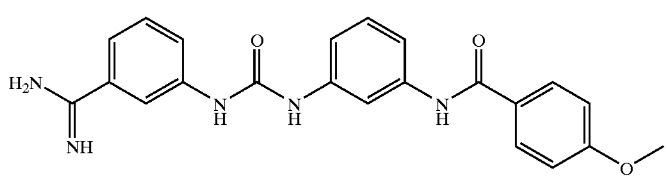 | 2 | 404[M + H] | A | | |
| 81 | 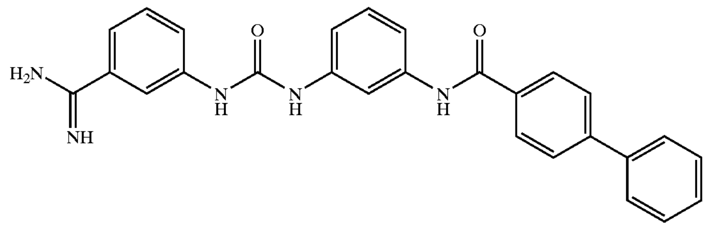 | 2a | 450[M + H] | B | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 82 | 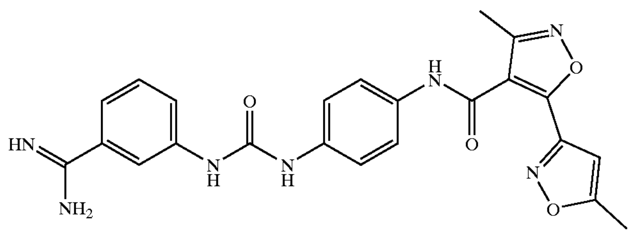 | 2a | 460[M + H] | B | | |
| 83 | 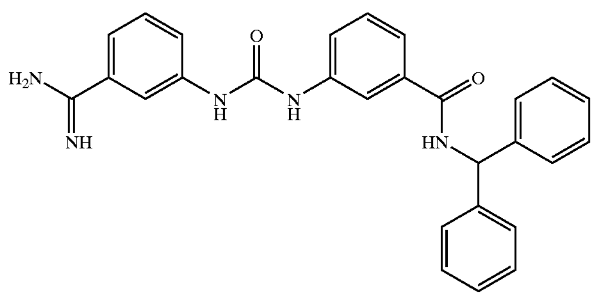 | 2 | 464[M + H] | B | | |
| 84 | 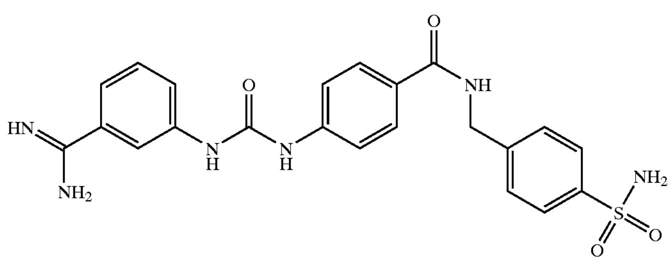 | 8 | 468[M + H] | B | | |
| 85 | 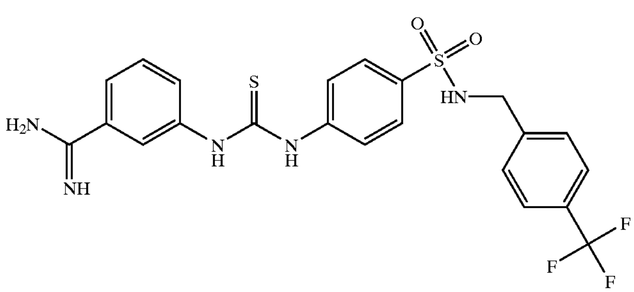 | 4a | 506[M − H] | A | | |
| 86 | 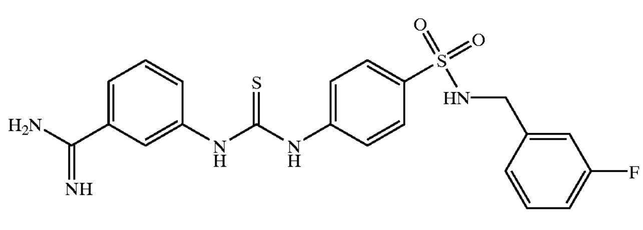 | 4a | 457[M − H] | A | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 87 | 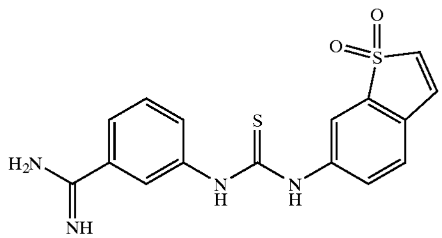 | 4a | 359[M + H] | A | | |
| 88 | 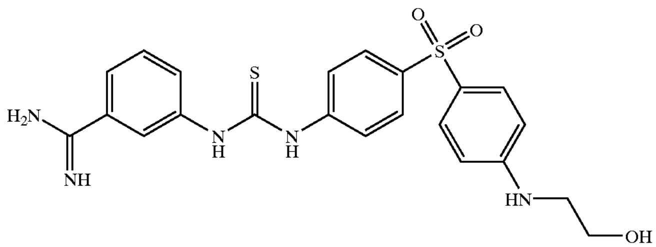 | 4a | 469[M − H] | B | | |
| 89 | 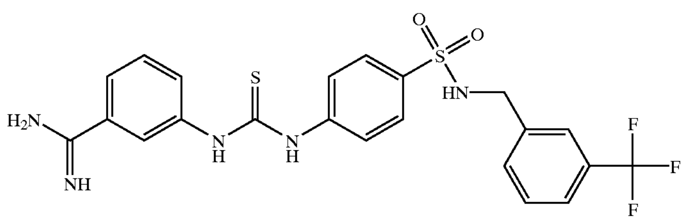 | 4a | 508[M + H]<br>506[M − H] | A | | |
| 90 | 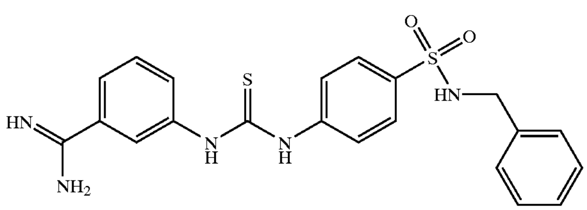 | 4a | 440[M + H] | | | A(50 μM) |
| 91 | 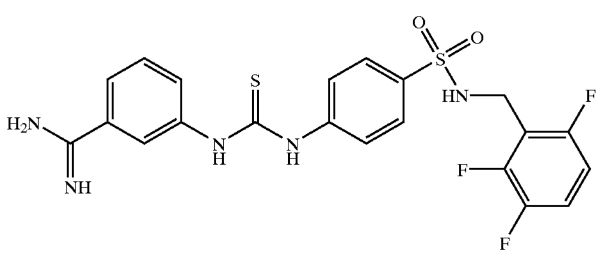 | 4a | 494[M + H] | | | A(50 μM)* |
| 92 | 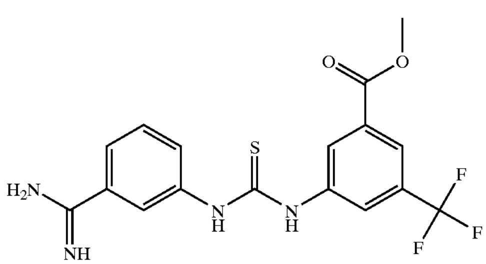 | 4a | 397[M + H] | A | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 93 | 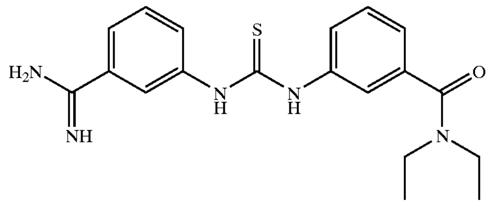 | 4a | 370[M + H] | A | | A(50 μM) |
| 94 | 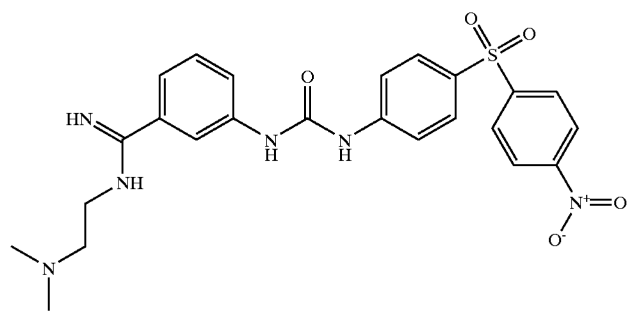 | 7 | 511[M + H]<br>509[M − H] | B | | |
| 95 | 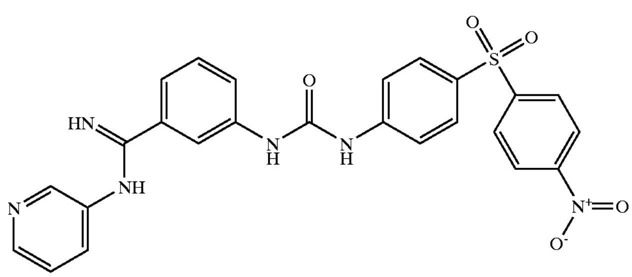 | 7 | 517[M + H] | A | | |
| 96 | 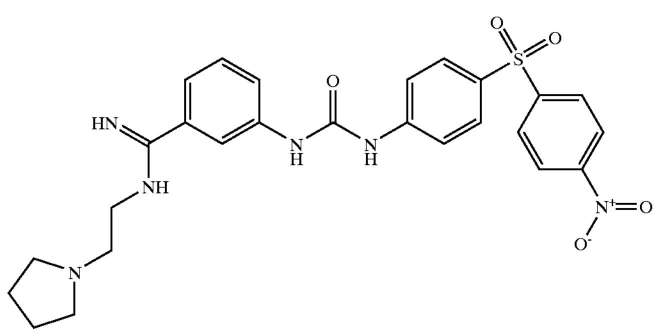 | 7 | 537[M + H]<br>536[M − H] | B | | |
| 97 | 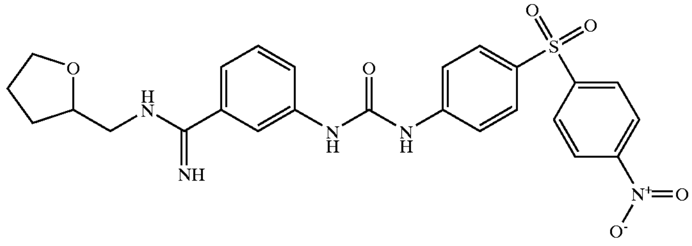 | 7 | 524[M + H]<br>522[M − H] | B | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 98 | 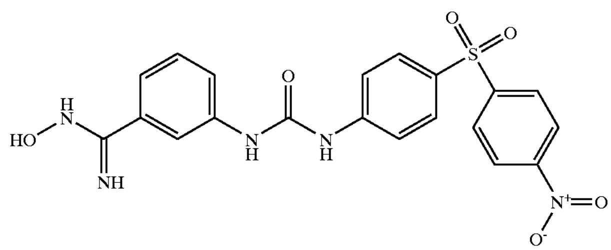 | 7 | 456[M + H]<br>454[M − H] | A | | |
| 99 | 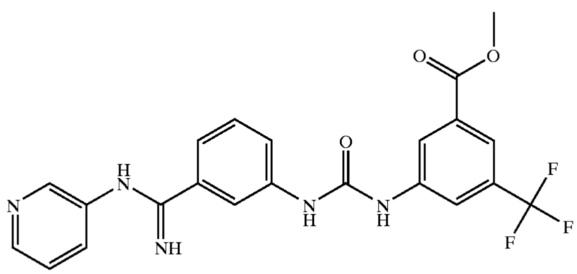 | 7 | 458[M + H] | B | | |
| 100 | 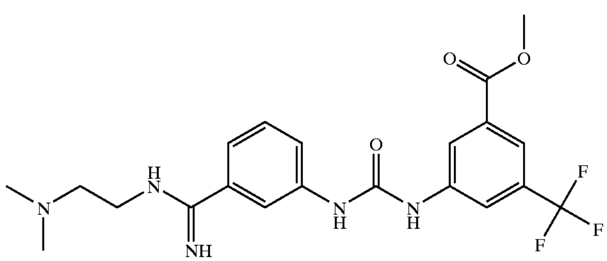 | 7 | 452[M + H] | B | | |
| 101 | 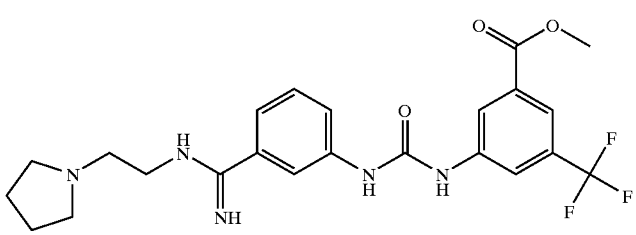 | 7 | 478[M + H] | B | | |
| 102 | 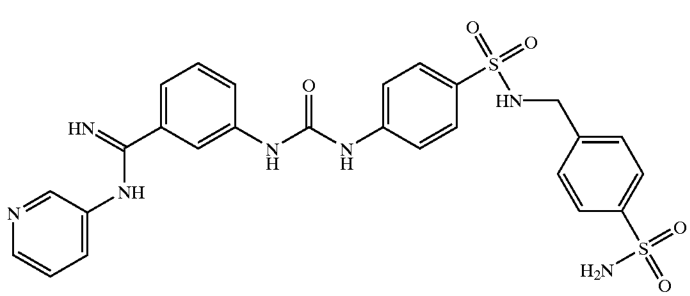 | 8 | 580[M + H]<br>578[M − H] | B | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 103 | 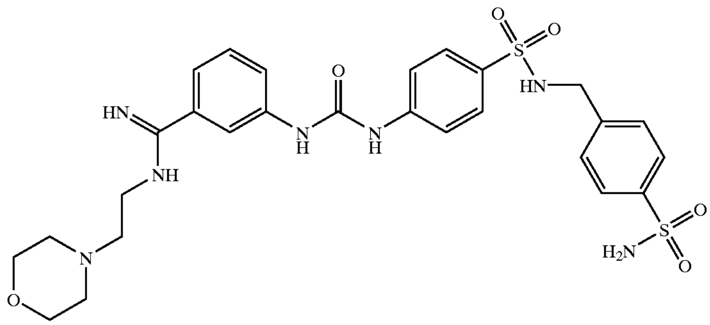 | 8 | 616[M + H]<br>614[M − H] | A | C | |
| 104 | 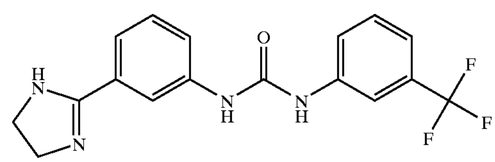 | 7 | 349[M + H]<br>347[M − H] | A | | B(5 μM) |
| 105 | 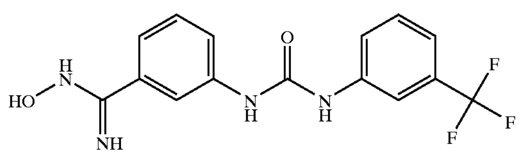 | 7 | 339[M + H]<br>337[M − H] | | | |
| 106 | 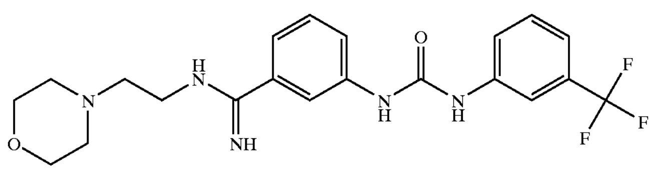 | 7 | 436[M + H]<br>434[M − H] | B | | |
| 107 | 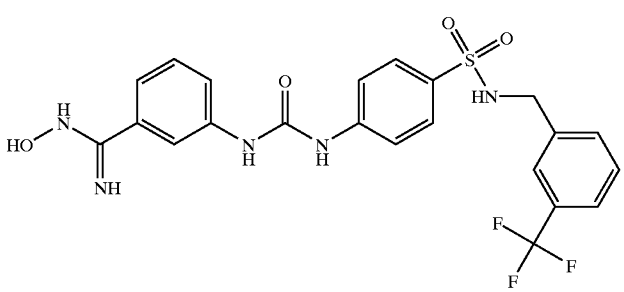 | 8 | 508[M + H]<br>506[M − H] | | | |
| 108 | 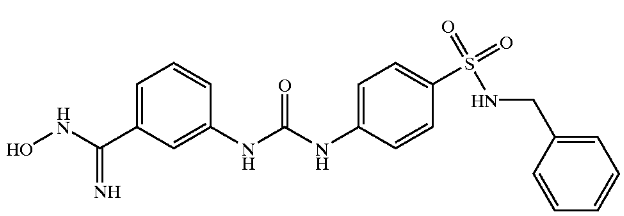 | 8 | 440[M + H] | | | |

TABLE 1-continued

| N. | structure | synthesis method | MS | anti-plasmodial activity (Dd2) | anti-plasmodial activity (3D7) | human proteasome inhibition |
|---|---|---|---|---|---|---|
| 109 | 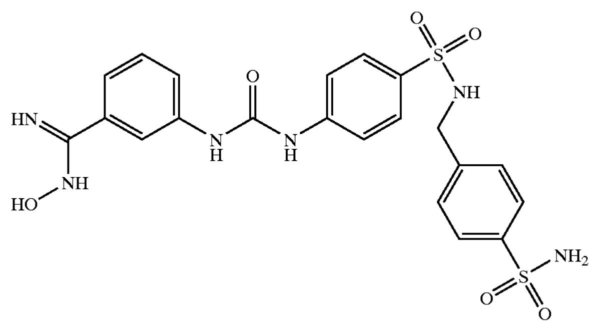 | 8 | 519[M + H]<br>517[M − H] | B | C | |
| 110 | 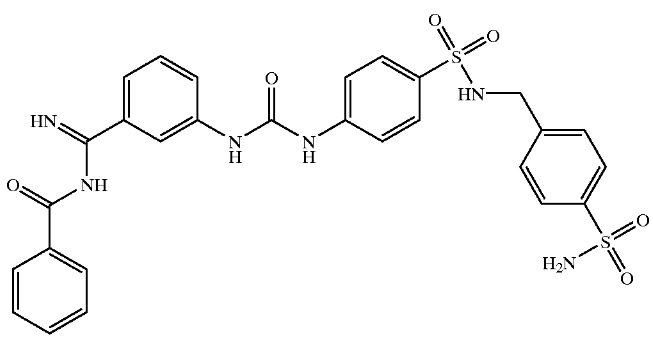 | 8 | 607[M + H]<br>605[M − H] | | | |
| 111 | 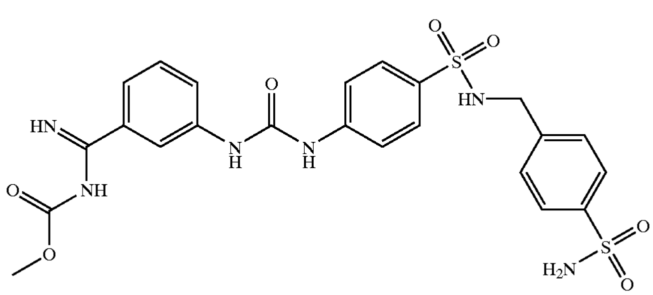 | 8 | 561[M + H] | | | |
| 112 | 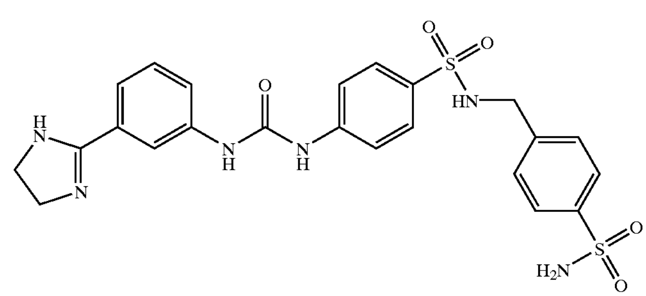 | 8 | 529[M + H]<br>527[M − H] | A | B | |

TABLE 1-continued

| N. | structure | synthesis method | MS | antiplasmodial activity (Dd2) | antiplasmodial activity (3D7) | human proteasome inhibition |
|---|---|---|---|---|---|---|
| 113 | 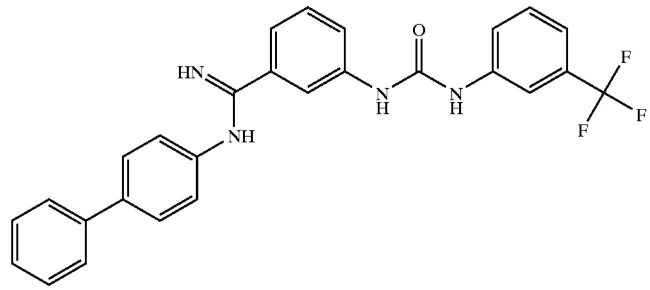 | 7 | 473[M − H]<br>475[M + H] | B | | |
| 114 | 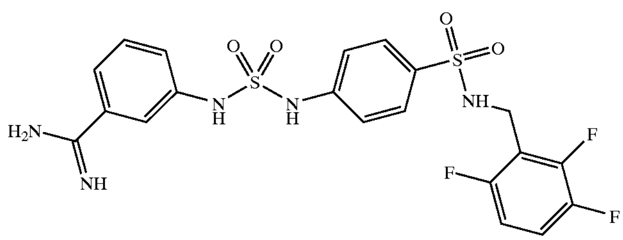 | | 514[M + H] | | | A(50 μM) |
| 115 | 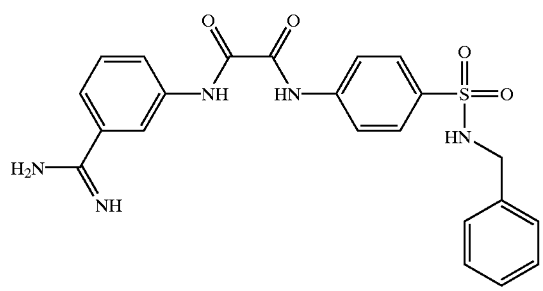 | 7 | 452[M + H] | B | | |
| 116 | 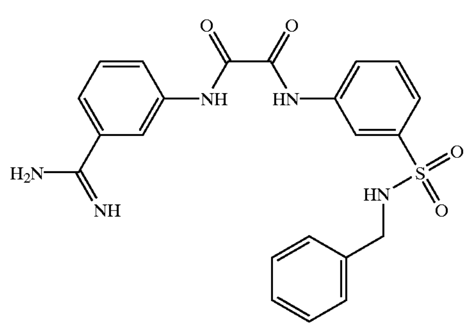 | 7 | 452[M + H] | C | | |

TABLE 2

| N | structure | 1H-NMR (D6-DMSO) | 13C-NMR |
|---|---|---|---|
| 24 | 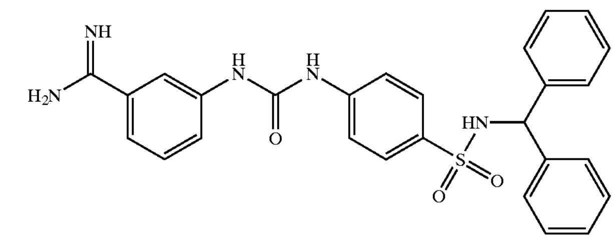 | 5.54(s, 1H, Ph₂CH), 7.11–7.21(m, 10H, Ar—H), 7.42(ddd, J=7.8, 1.8 and 1.1Hz, 1H, 4-H) 7.45–7.58(m, 5H, Ar—H), 7.69–7.78(ddd, J=8.1, 1.8 and 1.1Hz, 1H, 6-H), 8.02(t, J=1.8Hz, 1H, 2-H) | |
| 35 | 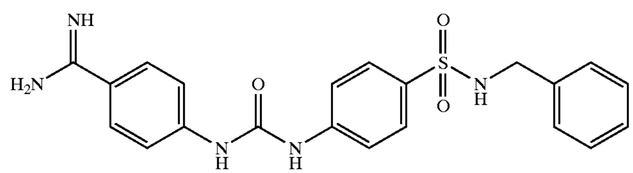 | 3.96(d, J=6.3, 2H, CH₂), 7.22–7.29(m, 5H, Ar—H), 7.64(d, J=8.9, 2H, Ar—H), 7.69(d, J=9.0, 2H, Ar—H), 7.74(d, J=9.0, 2H, Ar—H), 7.81(d, J=8.9, 2H, Ar—H), 8.0(t, J=6.3, 1H, N—H), 8.82(s, 2H, N—H), 9.18(s, 2H, N—H), 9.92(s, 1H, N—H), 10.00(s, 1H, N—H) | |
| 36 | 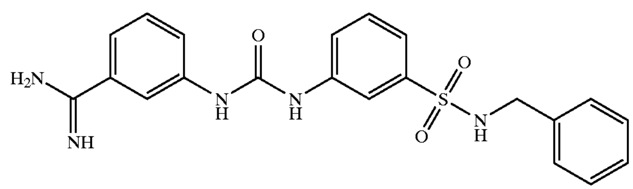 | 3.99(d, J=6.3, 2H, CH₂), 7.23–7.30(m, 5H, Ar—H), 7.36(d, J=8.3, 1H, Ar—H), 7.40–7.43(m, 1H, Ar—H), 7.47–7.56(m, 2H, Ar—H), 7.58–7.61(m, 1H, Ar—H), 7.72–7.75(m, 1H, Ar—H), 7.98(t, J=1.8, 1H, Ar—H), 8.12(t, J=6.3, 1H, N—H), 8.19(t, J=6.3, 1H, N—H), 9.00(s, 2H, N—H), 9.35(s, 2H, N—H), 9.77(s, 1H, N—H), 9.82(s, 1H, N—H) | |
| 37 | 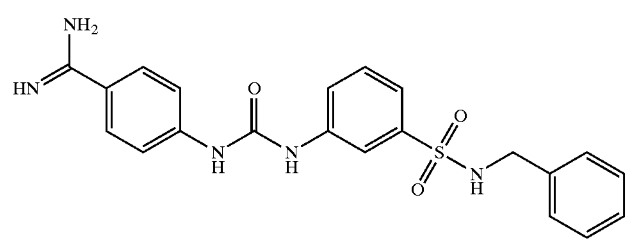 | 3.99(d, J=6.3, 2H, CH₂), 7.24–7.39(m, 5H, Ar—H), 7.42(d, J=7.9, 1H, Ar—H), 7.50(t, J=7.9, 1H, Ar—H), 7.59(d, J=7.9, 1H, Ar—H), 7.70(d, J=8.9, 2H, Ar—H), 7.81(d, J=8.9, 2H, Ar—H), 8.09(t, J=1.8, 1H, Ar—H), 8.12(t, J=6.3, 1H, Ar—H), 8.19(t, J=6.3, 1H, N—H), 8.83(s, 2H, N—H), 9.18(s, 2H, N—H), 9.85(s, 1H, N—H), 10.02(s, 1H, N—H) | |

TABLE 2-continued

| N | structure | 1H-NMR (D$_6$-DMSO) | 13C-NMR |
|---|---|---|---|
| 38 | 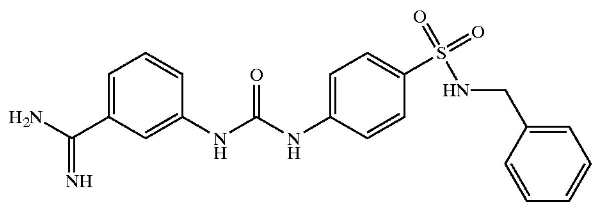 | 3.95(d, J=6.3, 2H, CH$_2$), 7.21–7.30(m, 5H, Ar—H), 7.37(d, J=8.1, 1H, Ar—H), 7.52(t, J=7.8, 1H, Ar—H), 7.64(d, J=9.0, 2H, Ar—H), 7.71–7.75(m, 3H, Ar—H), 7.95(t, J=2.1, 1H, Ar—H), 7.99(t, J=6.3, 1H, N—H), 9.13, (s, 2H, N—H), 9.38(s, 2H, N—H), 10.08(s, 1H, N—H), 10.23(s, 1H, N—H) | 46.5(CH$_2$), 117.4, 117.8, 121.8, 123.2, 127.4, 127.9, 128.2, 128.5, 129.5, 130.0, 133.5, 138.2, 140.5, 143.6 (C—Ar), 152.9(C=O), 166.6(C=N) |
| 40 | 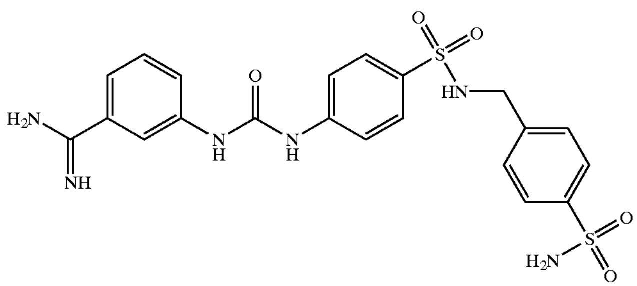 | 3.96(s, 2H, CH$_2$), 7.29–7.39(m, 3H, Ar—H), 7.45–7.50(m, 1H, Ar—H), 7.59–7.69(m, 7H, Ar—H), 7.89(s, 1H, Ar—H), 9.73(s, 1H, N—H), 9.88(s, 1H, N—H) | 45.9(CH$_2$), 117.4, 118.0, 121.2, 121.5, 125.9, 128.2, 129.3, 132.9, 133.2, 134.3, 139.9, 142.4, 143.3(C—Ar), 152.7(C=O), 164.6(C=N) |
| 41 | 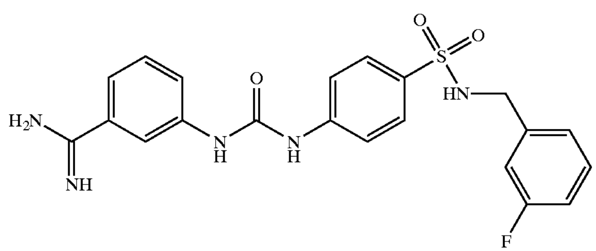 | 4.00(s, 2H, CH$_2$), 7.02–7.11(m, 3H, Ar—H), 7.29–7.34(m, 1H, Ar—H), 7.37(d, J=8.1, 1H, Ar—H), 7.54(t, J=8.1, 1H, Ar—H), 7.65(d, J=9.0, 2H, Ar—H), 7.70–7.76(m, 3H, Ar—H), 7.96(s, 1H, Ar—H), 9.26(s, br, 3H, N—H), 10.13(s, 1H, N—H), 10.28(s, 1H, N—H) | |
| 42 | 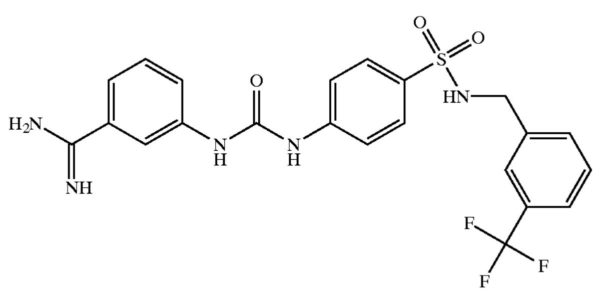 | 4.10(s, 2H, CH$_2$), 7.38(d, J=8.4, 1H, Ar—H), 7.51–7.58(m, 5H, Ar—H), 7.63(d, J=9.1, 2H, Ar—H), 7.70–7.76(m, 3H, Ar—H), 7.96(s, 1H, Ar—H), 9.24(s, br, 3H, N—H), 10.03(s, 1H, N—H), 10.18(s, 1H, N—H) | |

TABLE 2-continued

| N | structure | 1H-NMR (D₆-DMSO) | 13C-NMR |
|---|---|---|---|
| 43 | 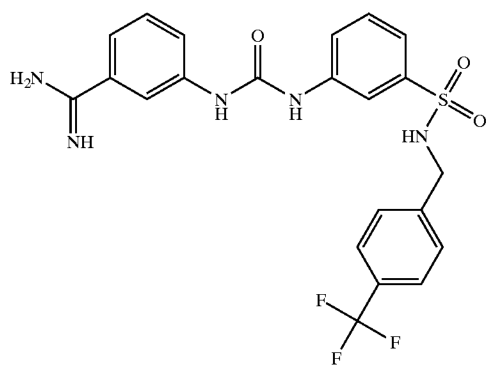 | 4.14–4.16(d, 2H, CH₂); 7.40–7.81(m, 10H, Ar); 8.02(s, 1H, o-Ar); 8.15(s, 1H, o-Ar); 8.40(t, 1H, NH), 9.11(s, 2H, NH); 9.42(s, 2H, NH); 9.03(s, 1H, NH); 9.98(s, 1H, NH) | |
| 44 | 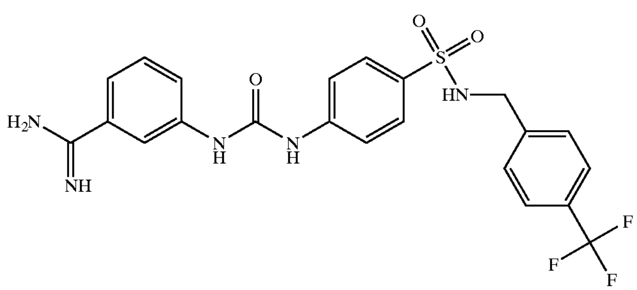 | 4.07(s, 2H, CH₂), 7.38(d, J=8.2, 1H, Ar—H), 7.48–7.57(m, 3H, Ar—H), 7.64–7.67(m, 4H, Ar—H), 7.72–7.77(m, 3H, Ar—H), 7.95(s, 1H, Ar—H), 9.18(s, br, 3H, N—H), 10.03(s, 1H, N—H), 10.19(s, 1H, N—H) | |
| 45 | 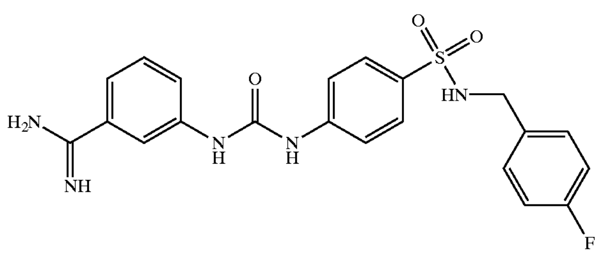 | 3.95(s, 2H, CH₂), 7.10(t, J=9.0, 2H, Ar—H), 7.28(dd, J=8.8, J=5.6, 2H, Ar—H), 7.37(d, J=8.3, 1H, Ar—H), 7.54(t, J=8.0, 1H, Ar—H), 7.65(d, J=9.1, 2H, Ar—H), 7.70–7.76(m, 3H, Ar—H), 7.96(s, 1H, Ar—H), 9.26(s, br, 3H, N—H), 10.09(s, 1H, N—H), 10.23(s, 1H, N—H) | |

TABLE 2-continued

| N | structure | 1H-NMR (D$_6$-DMSO) | 13C-NMR |
|---|---|---|---|
| 46 | 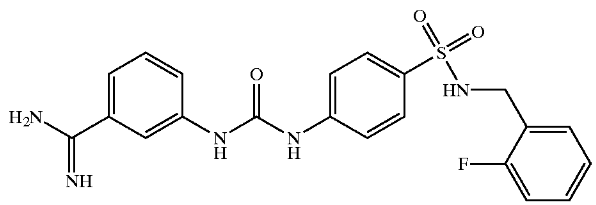 | 4.00(s, 2H, CH$_2$), 7.08–7.16(m, 2H, Ar—H), 7.28–7.39(m, 3H, Ar—H), 7.54(t, J=8.0, 1H, Ar—H), 7.65(d, J=8.9, 2H, Ar—H), 7.71–7.75(m, 3H, Ar—H), 7.96(s, 1H, Ar—H), 9.08(s, br, 3H, N—H), 9.82(s, 1H, N—H), 9.95(s, 1H, N—H) | |
| 47 | 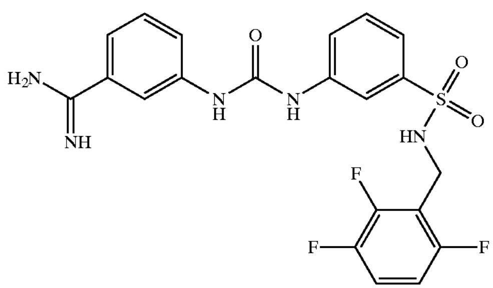 | 4.05–4.06(d, 2H, CH$_2$); 6.99–7.07(m, 1H, FAr); 7.33–7.74(m, 7H, Ar); 7.96(s, 1H, o-Ar); 8.05(s, 1H, o-Ar); 8.28(t, 1H, NH); 9.04(s, 2H, NH); 9.35(s, 2H, NH); 9.86(s, 1H, NH); 9.89(s, 1H, NH) | |
| 48 | 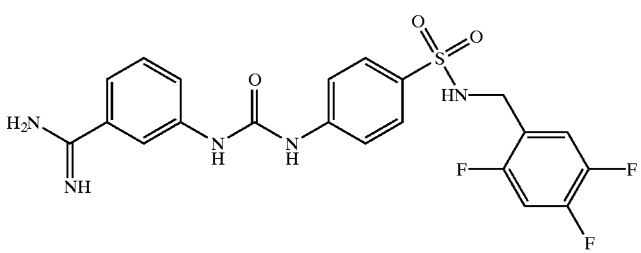 | 3.99(s, 2H, CH$_2$); 7.29–7.73(m, 10H, Ar); 7.95(s, 1H, Ar); 9.18(m br, 3H, C(NH)NH2); 9.69(s, 1H, NH); 9.82(s, 1H, NH) | |
| 49 | 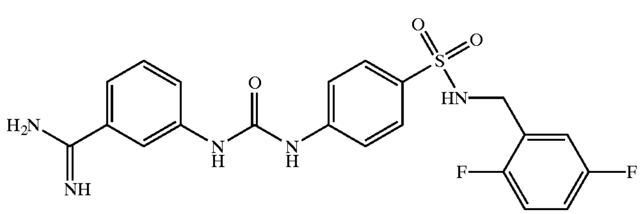 | 4.02(s, 2H, CH$_2$); 7.11–7.18(m, 3H, Ar—H), 7.37(d, J=8.3, 1H, Ar—H), 7.54(t, J=8.0, 1H, Ar—H), 7.63(d, J=9.1, 2H, Ar—H), 7.69–7.75(m, 3H, Ar—H), 7.96(s, 1H, Ar—H), 9.05(s, br, 3H, N—H), 9.83(s, 1H, N—H), 9.97(s, 1H, N—H) | |

TABLE 2-continued

| N | structure | 1H-NMR (D6-DMSO) | 13C-NMR |
|---|---|---|---|
| 50 | 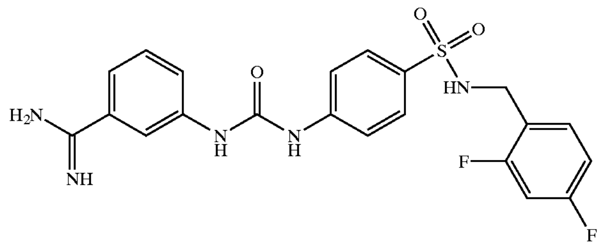 | 3.96(d, J=6.3, 2H, CH2), 7.98–7.05(dddd, J=8.5, J=8.5, J=2.5, J=1.0, 1H, Ar—H), 7.10–7.17(ddd, J=10.4, J=9.5, J=2.6, 1H, Ar—H), 7.33–7.41(m, 2H, Ar—H), 7.53(t, J=8.0, 1H, Ar—H), 7.63(d, J=9.1, 2H, Ar—H), 7.68–7.74(m, 3H, Ar—H), 7.95(t, J=1.8, 1H, Ar—H), 9.05(t, J=6.2, 1H, N—H), 8.98(s, 2H, N—H), 9.34(s, 2H, N—H), 9.77(s, 1H, N—H), 9.90(s, 1H, N—H) | |
| 51 | 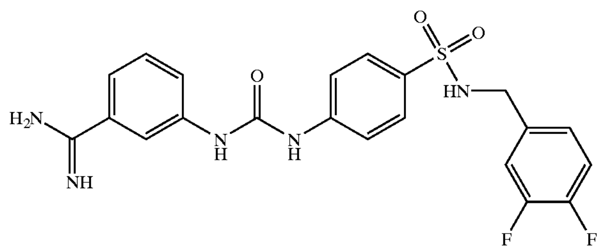 | 3.98(s, 2H, CH2), 7.09–7.12(m, 1H, Ar—H), 7.22–7.38(m, 3H, Ar—H), 7.54(t, J=8.0, 1H, Ar—H), 7.63(d, J=9.1, 2H, Ar—H), 7.69–7.75(m, 3H, Ar—H), 7.96(s, 1H, Ar—H), 9.10(s, br, 3H, N—H), 9.81(s, 1H, N—H), 9.95(s, 1H, N—H) | |
| 52 | 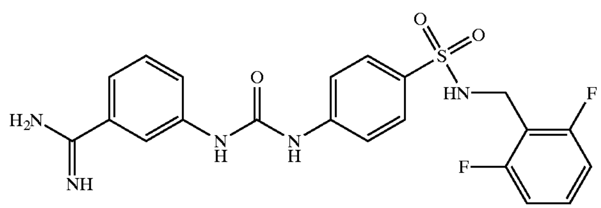 | 3.94(d, J=5.7, 2H, CH2), 6.97(t, J=8.0, 2H, Ar—H), 7.26–7.36(m, 2H, Ar—H), 7.49(t, J=8.0, 1H, Ar—H), 7.58(d, J=9.0, 2H, Ar—H), 7.65(d, J=9.0, 2H, Ar—H), 7.68–7.71(m, 1H, Ar—H), 7.91–7.94(m, 2H, Ar—H, N—H), 9.02(s, 2H, N—H), 9.32(s, 2H, N—H), 9.91(s, 1H, N—H), 10.05(s, 1H, N—H) | |
| 54 | 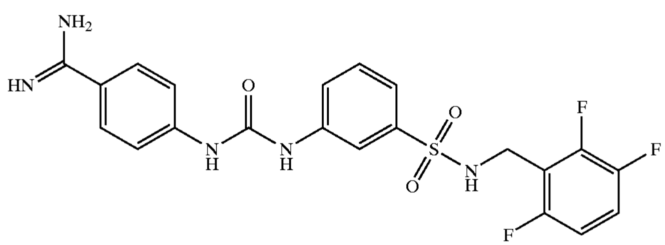 | 4.17(s, 2H, CH2), 6.99–7.07(m, 1H, Ar); 7.33–7.48(m, 3H, Ar); 7.55–7.57(m, 1H, Ar); 7.67–7.83(m, 4H, p-Ar); 8.04(s, 1H, o-Ar); 8.31(br, 1H, NH), 9.06(br, 4H, NH); 10.01(s, 1H, NH); 10.22(s, 1H, NH) | |

TABLE 2-continued

| N | structure | 1H-NMR (D₆-DMSO) | 13C-NMR |
|---|---|---|---|
| 55 | 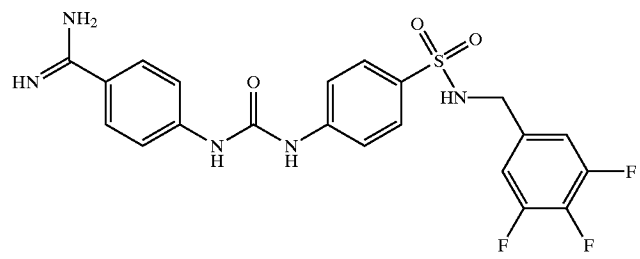 | 3.98(s, 2H, CH₂), 7.15(dd, J=9.0, J=6.9, 2H, Ar—H), 7.60–7.70(m, 6H, Ar—H), 7.82(d, J=7.8, 2H, Ar—H), 9.08(s, br, 3H, N—H), 10.26(s, 1H, N—H), 10.35(s, 1H, N—H) | |
| 56 | 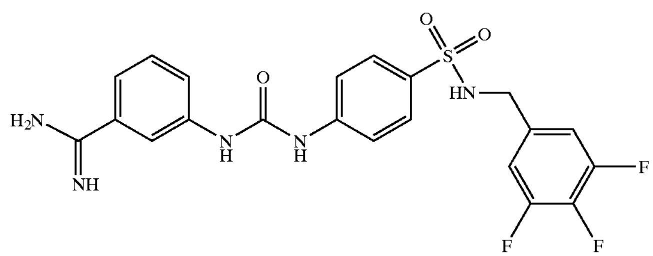 | 3.98(s, 2H, CH₂), 7.16(dd, J=8.9, J=6.9, 2H, Ar—H), 7.35(d, J=7.9, 1H, Ar—H), 7.52(t, J=8.0, 1H, Ar—H), 7.62(d, J=9.0, 2H, Ar—H), 7.71(d, J=9.0, 2H, Ar—H), 7.72–7.75(m, 1H, Ar—H), 7.94(s, 1H, Ar—H), 8.17(s, br, 1H, N—H), 9.28(s, br, 3H, N—H), 10.13(s, 1H, N—H), 10.30(s, 1H, N—H) | |
| 57 | 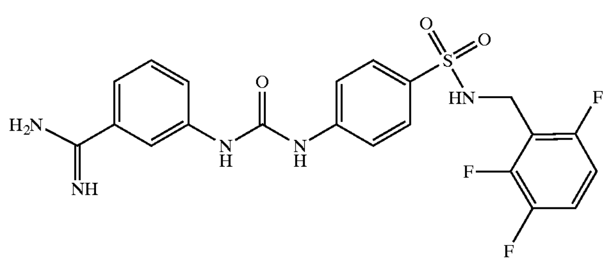 | 4.03(s, 2H, CH₂), 7.02–7.10(m, 1H, Ar), 7.35–7.76(m, 8H, Ar), 7.96(s, 1H, Ar), 8.10(s, br, 1H, NH), 9.01–9.28(m br, 3H, C(NH)NH2), 9.86(s, br, 1H, NH), 9.99(s, br, 1H, NH) | |

TABLE 2-continued

| N | structure | 1H-NMR (D$_6$-DMSO) | 13C-NMR |
|---|---|---|---|
| 60 | (3-fluorobenzyl sulfonamide linked via phenyl-NHC(O)NH-phenyl-C(=NH)NH$_2$) | 4.03(d, J=5.0, 1H, CH$_2$), 7.02–7.12(m, 3H, Ar—H), 7.29–7.33(m, 1H, Ar—H), 7.39–7.43(m, 1H, Ar—H), 7.49(t, J=7.9, 1H, Ar—H), 7.57–7.68(m, 1H, Ar—H), 7.70(d, J=8.9, 2H, Ar—H), 7.81(d, J=9.0, 2H, Ar—H), 8.10(s, 1H, Ar—H), 8.28(s, br, 1H, N—H), 8.84(s, br, 2H, N—H), 9.18(s, br, 2H, N—H), 9.87(s, 1H, N—H), 10.04(s, 1H, N—H) | |
| 62 | (4-sulfamoylbenzyl linked via SO$_2$NH-CH$_2$-phenyl-NHC(O)NH-phenyl-C(=NH)NH$_2$) | 4.02(s, 2H, CH$_2$), 7.41–7.75(m, 15H, Ar—H, N—H) | 45.6(CH$_2$), 117.4, 117.7, 125.5, 127.3, 127.69, 127.72, 129.3, 133.1, 140.9, 142.0, 143.0, 143.3(C—Ar), 152.1(C=O), 162.1(C=N) |
| 63 | (3-fluorobenzyl-NH-SO$_2$-phenyl-NHC(O)NH-phenyl-C(=NH)NH$_2$) | 4.00(s, 2H, CH$_2$), 7.01–7.11(m, 3H, Ar—H), 7.29–7.36(m, 1H, Ar—H), 7.62–7.74(m, 6H, Ar—H), 7.82(d, J=8.9, 2H, Ar—H), 8.09(s, 1H, N—H), 10.02(s, 1H, N—H), 10.10(s, 1H, N—H) | |

TABLE 2-continued

| N | structure | 1H-NMR (D6-DMSO) | 13C-NMR |
|---|---|---|---|
| 64 | (4-fluorobenzyl sulfonamide aryl urea benzamidine) | 3.95(d, J=5.5, 2H, CH2), 7.11(t, J=8.9, 2H, Ar—H), 7.28(dd, J=8.7, J=5.6, 2H, Ar—H), 7.63–7.84(m, 6-H, Ar—H), 7.83(d, J=8.9, 2H, Ar—H), 8.02(t, J=6.1, 1H, N—H), 8.95(s, 2H, N—H), 9.21(s, 2H, N—H), 10.21(s, 1H, N—H), 10.30(s, 1H, N—H) | |
| 65 | (2,6-difluorobenzyl sulfonamide aryl urea benzamidine) | 3.99(s, 2H, CH2), 7.01(t, J=8.0, 2H, Ar—H), 7.31–7.41(m, 1H, Ar—H), 7.49(d, J=8.7, 2H, Ar—H), 7.61(d, J=8.9, 2H, Ar—H), 7.67–7.74(m, 4H, Ar—H) | |
| 66 | (2,4-difluorobenzyl sulfonamide aryl urea benzamidine) | 3.98(s, 1H, CH2), 7.02(ddd, J=8.5, J=8.5, J=2.3, 1H, Ar—H), 7.11–7.18(ddd, J=9.8, J=9.8, J=2.5, 1H, Ar—H), 7.38(ddd, J=8.5, J=8.5, J=6.9, 1H, Ar—H), 7.62–7.73(m, 6H, Ar—H), 7.82(d, J=8.9, 2H, Ar—H), 8.02(s, br, 1H, N—H), 9.95(s, 1H, N—H), 10.02(s, 1H, N—H) | |
| 67 | (2,3,6-trifluorobenzyl sulfonamide aryl urea benzamidine) | 4.01(d, J=5.3, 2H, CH2), 7.01–7.07(m, 1H, Ar—H), 7.34–7.45(m, 1H, Ar—H), 7.61(d, J=8.9, 2H, Ar—H), 7.68(d, J=7.5, 4H, Ar—H), 7.81(d, J=8.9, 2H, Ar—H), 8.10(t, J=5.5, 1H, N—H), 8.92(s, 2H, N—H), 9.20(s, 2H, N—H), 10.13(s, 1H, N—H), 10.23(s, 1H, N—H) | |

TABLE 2-continued

| N | structure | 1H-NMR (D$_6$-DMSO) | 13C-NMR |
|---|---|---|---|
| 68 | 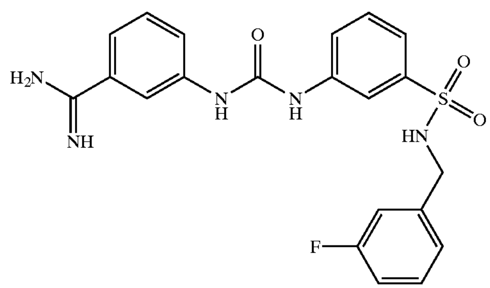 | 4.03(d, J=5.2, 2H, CH2), 7.02–7.12(m, 3H, Ar—H), 7.29–7.41(m, 3H, Ar—H), 7.46–7.59(m, 3H, Ar—H), 7.73(d, J=8.3, 1H, Ar—H), 7.98(s, 1H, Ar—H), 8.12(t, J=1.9, 1H, Ar—H), 8.27(m, br, 1H, N—H) 9.00(s, br, 2H, N—H), 9.35(s, br, 2H, N—H), 9.78(s, br, 2H, N—H) | |
| 69 | 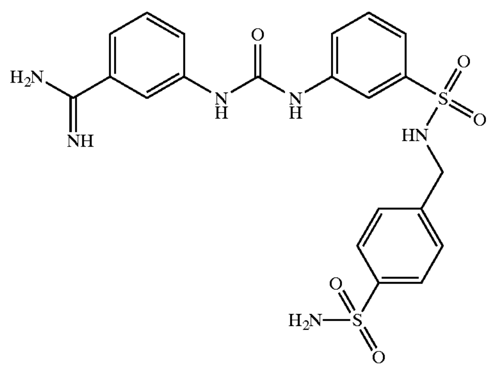 | 4.05(d, J=6.1, 2H, CH2), 7.33–7.51(m, 6H, Ar—H), 7.62(d, J=8.9, 1H, Ar—H), 7.73–7.76(m, 3H, Ar—H), 7.99(t, J=1.7, 1H, Ar—H), 8.17(t, J=1.9, 1H, Ar—H), 8.65(s, br, 4H, N—H), 10.4(s, br, 2H, N—H) | |
| 74 | 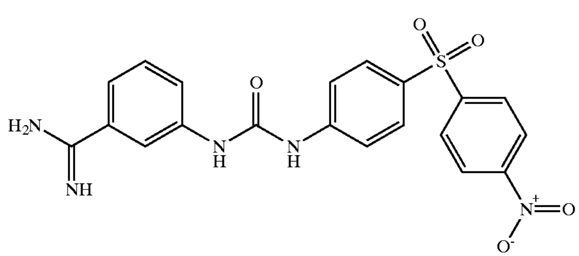 | 7.36(d, J=8.2, 1H, Ar—H), 7.51(t, J=8.0, 1H, Ar—H), 7.68–7.73(m, 3H, Ar—H), 7.92–7.95(m, 3H, Ar—H), 8.17(d, J=9.1, 2H, Ar—H), 8.38(d, J=9.1, 2H, Ar—H), 9.07(s, br, 3H, N—H), 9.72(s, br, 1H, N—H) | |

TABLE 2-continued

| N | structure | 1H-NMR (D6-DMSO) | 13C-NMR |
|---|---|---|---|
| 90 | 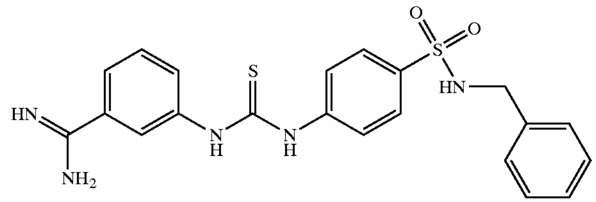 | 3.98–4.00(m, 2H, CH2); 7.23–7.32(m, 5H, Ar); 7.58–7.63(m, 2H, Ar); 7.76–7.89(m, 2H, Ar); 7.92–7.94(m, 3H, Ar); 8.06(s, 1H, Ar); 8.08–8.13(t, 1H, NH); 9.14–9.41(2s, br, 3H, C(NH)NH2); 11.03–11.18(2s, 2H, NH) | 46.03(Bz CH2); 121.99–142.95(C Aryl); 165.58(C(NH)NH2); 179.44(C=S) |
| 103 | 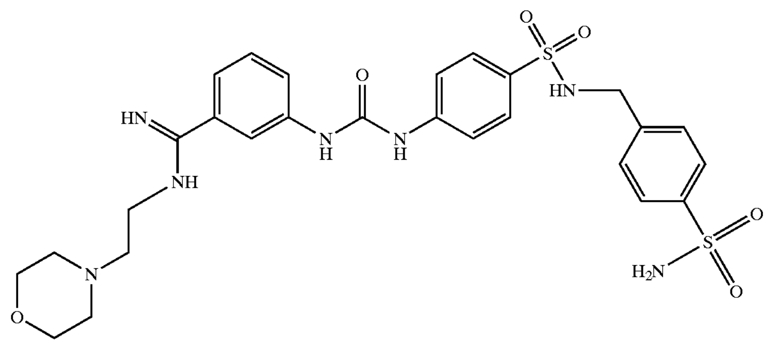 | 2.55(t, J=6.2, 2H, NCH2), 3.25(s, 4H, NCH2), 3.47(t, J=6.2, 2H, NCH2), 3.54(t, J=4.5, 4H, OCH2), 3.96(s, 2H, BnCH2), 7.22–7.39(m, 3H, Ar—H), 7.47(t, J=7.9, 1H, Ar—H), 7.58–7.69(m, 7H, Ar—H), 7.87(s, 1H, Ar—H), 9.27(s, br, 1H, N—H), 9.87(s, 1H, N—H), 10.00(s, 1H, N—H) | |
| 104 | 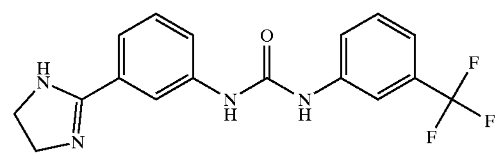 | 3.61(s, 4H, NCH2CH2N), 7.28–7.41(m, 3H, Ar—H), 7.47–7.53(m, 3H, Ar—H), 7.99, (s, 1H, Ar—H), 8.05(s, 1H, Ar—H), 9.61(s, 1H, N—H), 9.89(s, 1H, N—H) | |
| 107 | 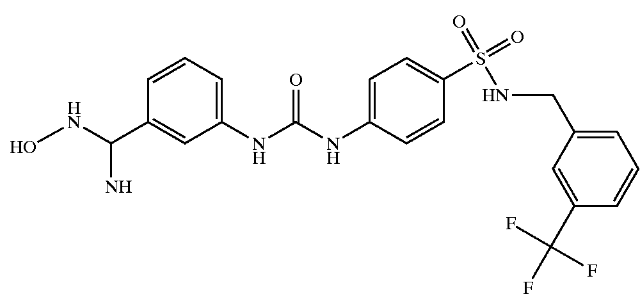 | 4.08(d, J=5.8, 2H, CH2), 5.73(s, 2H, N—H), 7.27–7.29(m, 2H, Ar—H), 7.46–7.51(m, 2H, Ar—H), 7.53–7.56(m, 3H, Ar—H), 7.60(d, J=9.0, 2H, Ar—H), 7.68(d, J=9.0, 2H, Ar—H), 7.77(s, 1H, Ar—H), 8.11, (t, J=6.1, 1H, N—H), 8.83(s, 1H, N—H), 9.09(s, 1H, N—H), 9.60, (s, 1H, O—H) | |

TABLE 2-continued

| N | structure | 1H-NMR (D₆-DMSO) | 13C-NMR |
|---|---|---|---|
| 109 | 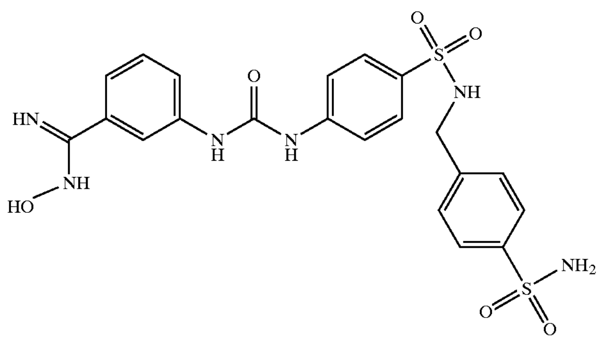 | 4.03(d, J=6.3, 2H, CH₂), 5.75(s, 2H, N—H), 7.29–7.31(m, 4H, Ar—H, NH₂), 7.43–7.52(m, 3H, Ar—H), 7.66(d, J=9.0, 2H, Ar—H), 7.73–7.79(m, 5H, Ar—H), 8.08(t, J=6.3, 1H, N—H), 8.87(s, 1H, N—H), 9.13(s, 1H, N—H), 9.62(s, 1H, O—H) | 45.7(CH₂), 115.9, 117.9, 119.3, 119.8, 125.8, 128.0, 128.7, 132.9, 134.3, 139.2, 142.2, 143.1, 143.7(C—Ar), 151.1(C=O), 152.4(C=N) |
| 112 | 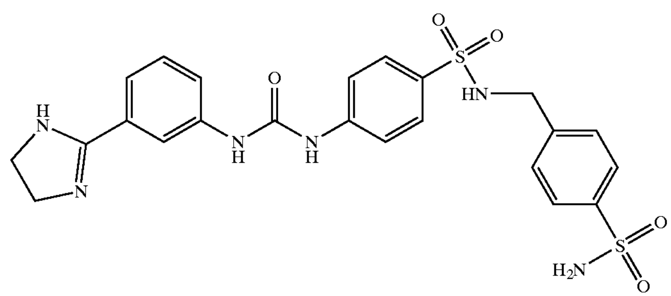 | 3.60(s, 4H, NCH₂CH₂N), 4.02(s, 2H, BnCH₂), 7.31–7.45(m, 5H, Ar—H), 7.56(m, 1H, Ar—H), 7.64–7.76(m, 6H, Ar—H), 7.95(s, 1H, Ar—H), 9.00(s, 1H, N—H), 9.23(s, 1H, N—H). | |
| 114 | 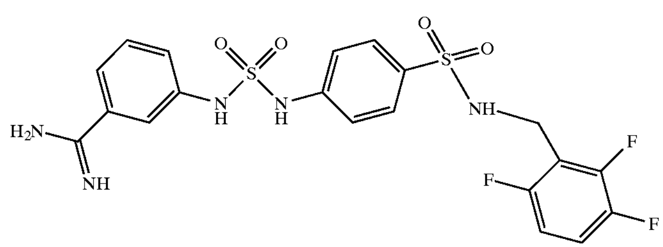 | 3.96(s, 2H, CH₂); 6.95–7.01(m, 1H, Ar—H); 7.25–7.60(m, 9H, Ar—H) | |

TABLE 2-continued

| N | structure | 1H-NMR (D₆-DMSO) | 13C-NMR |
|---|---|---|---|
| 115 | 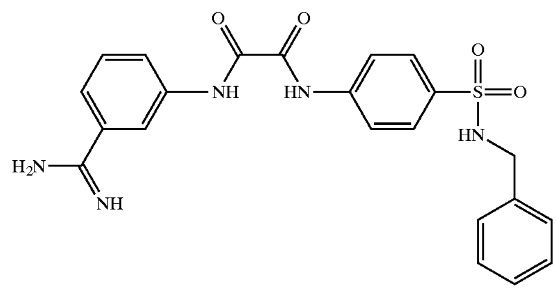 | 4.07(s, 2H, BnCH₂), 7.18–7.25(m, 5H, Ph), 7.59(dt, J=7.8 and 1.7Hz, 1H, 4-H), 7.64(t, J=7.8Hz, 1H, 5-H), 7.83(dt, J=9.0 and 2.1Hz, 2H, 3',5'-H), 7.96(dt, J=9.0 and 2.1Hz, 2H, 2',6'-H), 7.69(dt, J=7.6 and 1.7Hz, 1H, 6-H), 8.13(t, J=1.7Hz, 1H, 2-H) | 47.9(CH₂-Bn), 120.7(C-2), 121.5(C-2', 6'), 125.3(C-4), 126.9(C-6), 128.5(C-4''), 128.9, 129.1 and 129.4(C-3'',5'',2'',3''), 131.2(C-5), 130.6, 138.2, 138.6, 139.7 and 142.3(C-1,3,1',3',1''), 159.7 and 159.9(C=O), 168.6(C=NH) |
| 116 | 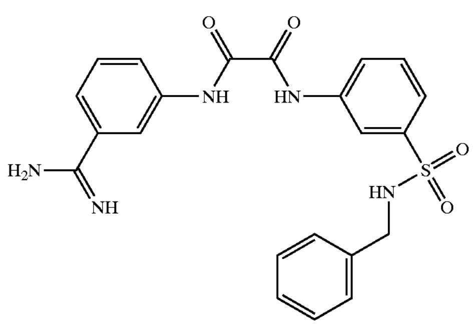 | 4.02(s, 2H, PhCH₂), 7.18–7.30(m, 5H), 7.54–7.66(m, 4H), 8.07–8.05(m, 1H), 8.17(dt, J=7.1 and 2.0Hz, 1H), (Ar—H), 8.29–8.31(m, 1H) and 8.44–846(m, 1H) (H-1 and H-1') | 46.1(CH₂-Ph), 118.5 and 119.9(C-1 and C-1'), 122.4, 124.0, 124.2, 125.2, 127.0, 127.5, 128.1, 129.0, 129.5, 129.6, 137.6, 138.0, 138.0 (C-aromatic), 158.6 and 158.6(O=C—N), 166.1(N=C—N) |

We claim:

1. A compound of the formula (I)

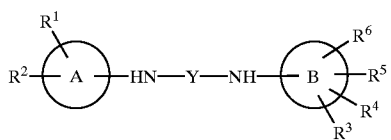

or a salt thereof, where
Y is C=O, C=S, C=NH, (C=O)$_2$ or SO$_2$
(A) and (B) are each independently a phenyl group
R$^1$ is

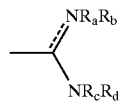

where R$_a$ and R$_c$ are each independently hydrogen, —O—(CO)—R' (where R' is as defined above), hydroxyl, hydroxyalkyl, haloalkyl, aminoalkyl, alkoxy, cyanoalkyl, alkyl or an unsaturated or saturated carbocyclic group selected from the group consisting of cyclopentyl, cyclohexyl, aryl, heteroaryl; R$_b$ is an optional substituent which may be independent of R$_a$ and R$_c$ and may be selected from the group as defined above for R$_a$ and R$_c$; R$_d$ is hydrogen or one of the following groups:

—(CO)—R$_e$ where R$_e$ is independently hydrogen, alkoxy, alkylthio, halogen, haloalkyl, haloalkyloxy, hydroxyalkyl, hydroxyalkylamino, alkyl, aryl, heteroaryl, amino, aminoalkyl or alkylamino group;

—(CH$_2$)$_n$-R$_f$ where R$_f$ is independently hydrogen, a hydroxy-alkyl, an alkyl, an allyl, an amino, an alkylamino, a morpholino, 2-tetrahydrofuran, N-pyrrolidino, a 3-pyridyl, a phenyl, a benzyl, a biphenyl or another heterocyclic group and n is 0, 1, 2 or 3;

—NR$_a$R$_b$ where R$_a$ and R$_b$ are defined above; or R$_a$ forms together with R$_d$ a 5- or 6- membered unsaturated or saturated heterocyclic ring which optionally has 0 to 3 substituents R''; the dotted line means a double bond unless there is a substituent R$_b$, in the formula of R$^1$ as defined above;

R'' is independently hydrogen, alkoxy, alkylthio, aminoalkyl, halogen, —CO$_2$R', —CR'O, haloalkyl, haloalkyloxy, —NO$_2$, —CN, hydroxyalkyl, alkyl, aryl, heteroaryl, amino, alkylamino or aminoalkyl group or a double bonded oxygen, wherein R' is as defined above;

R$^2$ is a hydrogen, a halogen, alkoxy, alkylthio, —CO$_2$R', —CR'O, haloalkyl, haloalkyloxy, —NO$_2$, —CN, hydroxy, hydroxyalkyl, alkyl, aryl, amino, alkylamino or an aminoalkyl group;

R$^3$ is a hydrogen, a halogen, haloalkyl, —NO$_2$, —CN, an alkyl or an aryl group;

R$^4$ is a hydrogen or a group capable of hydrogen bond formation except for a group as defined for substituent R$^1$;

R$^5$ is hydrogen or, independently of R$^4$, a group selected from the groups as defined above for R$^4$;

R$^6$ is hydrogen or, independently of R$^2$, a group selected from the groups as defined above for R$^2$; and with the proviso that a compound of the formula (I) is not a compound (a) in which Y is equal to C=O, both (A) and (B) are a phenyl group, and R$^1$ is the group

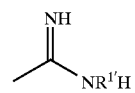

where R$^{1'}$ is hydrogen or phenyl, R$^2$, R$^3$, R$^5$, and R$^6$ are identical and are hydrogen and R$^4$ is phenyl, benzyl, phenoxy, chloro or a dimethylamino group in the 3- or 4-position to the NH—Y—NH group of formula(I); or (b) in which (A) and (B) are phenyl and R$^4$, R$^5$ or R$^6$ are in the ortho-position to the NH—Y—NH group of formula (I).

2. The compound according to claim 1 with the proviso that the compounds of the formula (I) are not compounds in which Y is equal to C=O, (B) is a benzofuranyl, dibenzofuranyl, 1-alkylindol or aryl (optionally substituted by alkyl, halogen, trihaloalkoxy or N,N-dialkylamino) and R$^1$ is the group

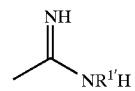

where R$^{1'}$ is hydrogen, alkyl, acyl, aryl, 1-alkylindolyl or alkylthio.

3. The compound according to claim 1, wherein R$^2$, R$^3$, R$^5$, and/or R$^6$ hydrogen.

4. The compound according to claim 1, wherein R$^1$ is an optionally substituted or cyclic amidine.

5. The compound according to claim 1, wherein R$_a$ and/or R$_c$ are hydrogen and/or R$_b$ is not present.

6. The compound according to claim 1, wherein R$^4$ is an arylsulphone, sulphonamide, alkylsulphonamide, arylsulphonamide, alkylsulphone or arylalkylsulfonamide where the substituents are independently one or more of the following groups: hydrogen, halogen, haloalkyl, haloalkoxy, CONRR', SO$^2$NRR', CO$_2$R and sulphonamide, where R and R' independently are as defined above.

7. The compound according to claim 1 as a medicament.

* * * * *

UNITED STATES PATENT AND TRADEMARK OFFICE
CERTIFICATE OF CORRECTION

PATENT NO. : 6,949,567 B2
APPLICATION NO. : 10/083008
DATED : September 27, 2005
INVENTOR(S) : Aschenbrenner et al.

Page 1 of 1

It is certified that error appears in the above-identified patent and that said Letters Patent is hereby corrected as shown below:

Column 9, Line 63, replace "chlorosylfony- " with --chlorosulfonuyl- --

Column 15,
Line 13, replace "congolense" with --*congolense*--;
Line 13, replace "gambiense" with --*gambiense*--;
Line 16, replace "*leishmania*" with --leishmania--;
Line 20, replace "congolense" with --*congolense*--;
Line 21, replace "brucei" with --*brucei*--; and
Line 21, replace "*Nagana cattle*" with --Nagana cattle--.

Column 22, Line 48, replace "benzamidine" with --benzamidine.--

Column 86, in Table 2, entry "107", replace

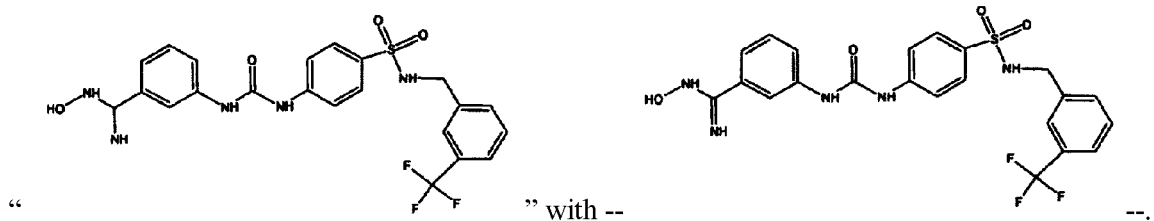

" with -- -- .

Signed and Sealed this

Twenty-sixth Day of September, 2006

JON W. DUDAS
*Director of the United States Patent and Trademark Office*